United States Patent [19]

Baschang et al.

[11] Patent Number: 4,574,058

[45] **Date of Patent: * Mar. 4, 1986**

[54] ANTIGEN DERIVATIVES AND PROCESSES FOR THEIR PREPARATION

[75] Inventors: Gerhard Baschang, Bettingen; Felix M. Dietrich, Basel; Roland Gisler, Binningen, all of Switzerland; Albert Hartmann, Grenzach, Fed. Rep. of Germany; Jaroslav Stanek, Birsfelden, Switzerland; Lajos Tarcsay, Grenzach-Wyhlen, Fed. Rep. of Germany

[73] Assignee: Ciba-Geigy Corporation, Ardsley, N.Y.

[ * ] Notice: The portion of the term of this patent subsequent to Aug. 9, 2000 has been disclaimed.

[21] Appl. No.: 477,281

[22] Filed: Mar. 21, 1983

Related U.S. Application Data

[60] Continuation of Ser. No. 303,244, Sep. 17, 1981, Pat. No. 4,397,844, which is a division of Ser. No. 14,190, Feb. 22, 1979, abandoned.

[30] Foreign Application Priority Data

| | | | |
|---|---|---|---|
| Feb. 24, 1978 | [CH] | Switzerland | 2035/78 |
| Apr. 7, 1978 | [CH] | Switzerland | 3777/78 |
| May 18, 1978 | [CH] | Switzerland | 5394/78 |

[51] Int. Cl.⁴ .......... C07C 103/52
[52] U.S. Cl. .......... 260/112.5 R
[58] Field of Search .......... 424/177; 260/112.5 R

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,153,684 | 5/1979 | Audibert et al. | 424/88 |
| 4,186,194 | 1/1980 | Adam et al. | 424/89 |
| 4,220,637 | 9/1980 | Audibert et al. | 424/88 |
| 4,235,771 | 11/1980 | Adam et al. | 260/112.5 R |
| 4,272,524 | 6/1981 | Cludid et al. | 424/177 |
| 4,327,085 | 4/1982 | Audibert et al. | 424/177 |
| 4,397,844 | 8/1983 | Baschang et al. | 424/177 |

FOREIGN PATENT DOCUMENTS

| | | |
|---|---|---|
| 2089326 | 7/1972 | France . |
| 2319373 | 2/1977 | France . |
| 2355505 | 1/1978 | France . |
| 1279213 | 7/1972 | United Kingdom . |

OTHER PUBLICATIONS

Chem. Abst., 86, 155,893t.
Chem. Abst., 90, 34,099.

*Primary Examiner*—Delbert R. Phillips
*Attorney, Agent, or Firm*—Irving N. Feit; Irving M. Fishman

[57] ABSTRACT

The invention relates to novel antigen derivatives comprising an antigen and at least one muramylpeptide covalently bonded thereto, if appropriate via a spacer, to pharmaceutical preparations which contain such compounds and to their use as a vaccine.

The novel antigen derivatives produce a pronounced increase in the immuno-response to the antigen, and in particular also a cell-medicated immunity under clinically acceptable conditions of administration.

15 Claims, No Drawings

ANTIGEN DERIVATIVES AND PROCESSES FOR THEIR PREPARATION

This is a continuation of application Ser. No. 303,244 filed Sept. 17, 1981, now U.S. Pat. No. 4,397,844, which is a division of application Ser. No. 014,190, filed Feb. 22, 1979, now abandoned.

The invention relates to novel antigen derivatives, to processes for their preparation, to pharmaceutical preparations which contain these novel antigen derivatives, and to their use for stimulating immunity, and also to novel intermediates and their preparation.

The invention in particular relates to novel antigen derivatives comprising an antigen and at least one muramyl-peptide covalently bonded thereto, if appropriate via a bridge member. These novel antigen derivatives can for example be more closely characterised by the formula (I)

$$A-[Z_{o\text{-}1}-MP]_n \qquad (I)$$

in which A is the radical of an antigen, Z is a bridge member (spacer), MP is the radical of a muramyl-peptide and n is an integer greater than 0.

An antigen is to be understood as meaning an organic substance which is recognised by the physiological medium, i.e. by the human or animal organism, as being immunologically foreign, or which can be recognised as foreign under certain preconditions.

The antigens primarily comprise all substances which bring about the specific immunisation of a living organism against infectious pathogens or undesired reactions, such as allergic sensitisation or rejection of transplanted foreign tissue. In particular, the definition includes antigens as ingredients of vaccines.

Relevant vaccines are, firstly, those which can be employed in classical inoculation methods for specific immunological protection against infectious diseases. Suitable antigens, which are contained in such vaccines, are the attenuated living or killed, modified or degraded pathogens of infectious diseases, the toxoids formed by thee pathogens or natural or synthetically prepared partial components of pathogens and toxoids. Specific examples of classes of pathogens are viruses, Chlamydia, Rickettsia, bacteria, protozoa and metazoic parasites. Preferred antigens are those which, when administered as constituents of vaccines, are suitable for the treatment of, for example, influenza A and B, parainfluenza 1-3, respiratory diseases caused by respiratory syncytial virus, rhinoviruses or adenoviruses, cytomegaly, rubella, measles, mumps, whooping cough, poliomyelitis, Herpes simplex 1 and 2, chickenpox, Herpes zoster, rotavirus diseases, hepatitis A, B and others, rabies, foot and mouth disease, trachoma, caries, meningites caused by meningococci A, B and C, diseases caused by pneumococci, H. influenzae, streptococci (in particular rheumatic fever), Pseudomonas and Proteus, typhus, paratyphus and other diseases caused by enterobacteriaceae and characterised by diarrhoea, gonorrhoea, syphilis, malaria, trypanosomiases (sleeping sickness and Chagas disease), leishmanioses, filarioses, schistosomiases, ankylostomiases and other diseases caused by worms.

Secondly, mention must be made of novel vaccines which are not directed against pathogens of infectious diseases, but either against constituents innate in the body, i.e. normal and aberrant auto-antigens, or against sensitising environmental antigens, i.e. allergens.

In the one case, attempts are made, by immunisation against normal or abnormal auto-antigens, to eliminate the function of molecules innate in the body, (for example of hormones, of other mediators and of humoral and cell-located receptors) or to cancel out the spread or persistence of abnormal, in particular neoplastic cell lines. Preferred antigens, as constituents of such vaccines, are, for example, partial sequences of human choriongonadotropin or constituents of spermatozoa for immunisation against mediators of fertility and hence for the immunological elimination of reproductive functions; mediators of inflammatory processes, in particular in a purified form, including the lymphokines secreted by lymphocytes, especially MIF (macrophage migration inhibitory factor) for the immunological suppression of inflammatory diseases; immunologically specific antigen receptors of lymphocytes and of antibodies (fractionated antigen-specific lymphocytes, antigen receptors extracted from, or excreted by, these lymphocytes, and fractionated antigen-specific antibodies or antibody fragments) for anti-idiotype immunisation (immunisation against the auto-antigens characteristic of the antigen receptor structures) with the object of cutting out specific immuno-reactions in order to eliminate immuno-processes causing illness, such as auto-immunity (for example against synovial antigens and immunoglobulins in primary chronic polyarthritis, against myelin components in degenerative diseases of the central nervous system, against TSH receptors in auto-immune thyreoiditis, against acetylcholine receptors of cross-striated muscles in myasthenia gravis, against insular cell components in juvenile diabetes and the like) or allergy (for example against grass pollen, dusts or medicaments in the case of allergic asthma, allergic rhinitis and hypersensitivity to medicaments) or to avoid innately normal, but undesirable immuno-reactions (for example induction of immuno-tolerance to prevent the rejection of transplanted foreign organs and tissues); and autologous tumour cells, tumour cell fragments or tumour membrane components, or homologous or heterologous cells, cell fragments or components which give a cross-reaction with these, including oncornavirus-coded glycoproteins, such as GP 70, for tumour-specific immunisation within the scope of prophylaxis and therapy of cancer diseases.

In the other case, attempts are made, by immunisation against allergens, to induce, in place of the pathogenetically relevant IgE antibody response, predominantly, and to a sufficient degree, IgG and IgA antibodies against the sensitising environmental antigens, and thereby to trap allergens, in the circulation and in the secretions, by means of specific antibodies before they can react with the IgE antibodies bonded to mast cells and can thereby trigger the liberation of allergic mediators. In this antigen-specific desensitisation, the allergens, i.e., for example grass pollen, dusts or medicaments, are themselves antigen constituents of the vaccines.

It is entirely possible, and even advantageous, for antigens, especially if they are of low molecular weight, to be covalently bonded to a high molecular weight carrier. Examples of carriers are, in particular, polymers of lactic acid and of its derivatives, which possess a free carboxyl group at the chain end, such as their esters with glycollic acids, poly(lactic acid amides), or lactic acid polyester-amides, for example those described in British patent specification No. 932,382, as well as alginic acid, polygalacturonic acid, pectic acid, carboxymethylcellulose or agarose. Further possible carriers are basic, neutral or acidic polyaminoacids which are not themselves immunogenic, such as polyaspartic acid, polyglutamic acid, polylysine or polyornithine. Further suitable carriers are any other antigens, in the sense of the definition given above or of the examples listed above, provided an immuno-reaction against these can be tolerated or may even be desirable. For example, an HCG-peptide may be covalently bonded to tetanus toxoid as the carrier.

Muramyl-peptides are in particular synthetically preparable compounds of the general formula II

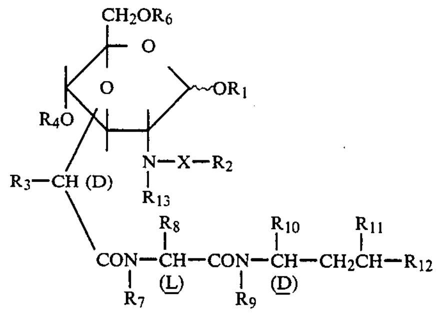

(II)

in which X is a carbonyl, carbonyloxy or sulfonyl group, $R_1$ is hydrogen, alkyl, unsubstituted or substituted benzyl or acyl, $R_2$ is unsubstituted or substituted alkyl or carbocyclic aryl, $R_4$ and $R_6$ independently of one another are hydrogen, alkyl, unsubstituted or substituted benzyl or acyl, $R_3$ is hydrogen or alkyl, $R_7$ and $R_{13}$ are hydrogen or lower alkyl, $R_8$ is hydrogen, lower alkyl, free, esterified or etherified hydroxy-lower alkyl, free, esterified or etherified mercapto-lower alkyl, free or acylated amino-lower alkyl, cycloalkyl having 5 or 6 carbon atoms, cycloalkyl-lower alkyl, or which the cycloalkyl radical contains 5 or 6 carbon atoms, unsubstituted or substituted aryl or aralkyl, or nitrogen-containing heterocyclyl or heterocyclyl-lower alkyl, $R_7$ and $R_8$ together can also be alkylene having 3 or 4 carbon atoms, $R_9$ is hydrogen or lower alkyl, the radicals $R_{10}$, $R_{11}$ and $R_{12}$ independently of one another are a carboxyl radical which may or may not be esterified or amidised, and $R_{11}$ can also be hydrogen, or $R_1$, $R_4$ and $R_6$ are tri-lower alkylsilyl, especially trimethylsilyl, or oligomers thereof, as described, for example, in German Offenlegungsschrift No. 2,450,355 and obtainable by isolation from micro-organism cell walls.

The various parts of the novel compounds are covalently bonded to one another, i.e. the antigen is bonded by one or more of its functional groups, via a link usually encountered in peptide chemistry, to the radical of the muramyl-peptide, either directly or via a bridge member (spacer).

Suitable bridge members (spacers) are in particular bivalent radicals of aliphatic compounds, for example of compounds which possess at least two amino groups, at least one amino group and one carboxyl or thiocarboxyl group, or at least two carboxyl or thiocarboxyl groups, for example aliphatic diamines, aminothiocarboxylic acids, neutral, basic or acidic aminoacids, dipeptides or oligopeptides.

Spacers are in particular $\alpha,\omega$-diaminoalkanes, especially $\alpha,\omega$-diamino-lower alkanes, for example ethylenediamine, propylenediamine and tetramethylenediamine, alkyl-dicarboxylic acids, for example succinic acid or glutaric acid and $\alpha$-, $\beta$- or $\gamma$-aminoalkanecarboxylic acids, preferably $\alpha$-amino-lower alkanecarboxylic acids, especially the natural $\alpha$-amino-lower alkanecarboxylic acids, such as glycine, $\beta$-alanine, L-alanine, $\alpha$-amino-isobutyric acid, valine or leucine.

Particularly preferred covalent linking structures are carboxylic acid ester, carboxylic acid amide, thiocarboxylic acid ester or thiocarboxylic acid amide groups.

The novel compounds mentioned may contain several covalent linking structures, depending on the nature of the spacers used. Accordingly, the above formula I can, for example, have the following more detailed form

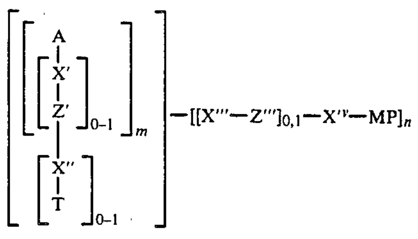

(III)

in which A is the radical of the antigen, T is the radical of the carrier, MP is the radical of the muramyl-peptide, Z' and Z''' are bivalent spacers and X', X'', X''' and X'v are covalent linking structures, and m and n are integers greater than 0.

Alkyl is straight-chain or branched alkyl bonded in any desired position and having up to 18 carbon atoms, but is in particular lower alkyl.

Suitable substituents of an alkyl group which can be substituted are in particular free or functionally modified hydroxyl or mercapto groups, such as etherified or esterified hydroxyl or mercapto groups, for example lower alkoxy or lower alkylmercapto groups, or halogen atoms, or free or functionally modified carboxyl groups, such as carbo-lower alkoxy groups or carbamoyl groups. The substituted alkyl radical, such as lower alkyl radical, can carry one substituent or two or more identical or different substituents, in particular free hydroxyl groups or halogen atoms.

Carbocyclic aryl radicals are in particular monocyclic, but also bicyclic, aryl radicals, especially phenyl but also naphthyl. They may be unsubstituted or be monosubstituted, disubstituted or polysubstituted, for example by lower alkyl groups, free, etherified or esterified hydroxyl, for example lower alkoxy or lower alkylenedioxy or halogen atoms, and/or trifluoromethyl groups.

Aralkyl is in particular aryl-lower alkyl, wherein aryl has the above meaning. In particular, aryl-lower alkyl is benzyl or phenylethyl, in which the phenyl nucleus may be monosubstituted, disubstituted or polysubstituted.

Substituted or unsubstituted benzyl radicals are in particular those benzyl radicals which are unsubstituted or are monosubstituted, disubstituted or polysubstituted in the aromatic nucleus, for example by lower alkyl or free, etherified or esterified hydroxyl or mercapto groups, for example lower alkoxy, lower alkylenedioxy, lower alkylmercapto or trifluoromethyl groups and/or halogen atoms.

Nitrogen-containing heterocyclyl is in particular the radical of a 5-membered or 6-membered heterocyclic compound containing one or two nitrogen atoms in the ring. The radical can be unsaturated or saturated and can, for example, contain a fused phenyl radical. Examples of such radicals are the pyrrole, indane, pyridyl or imidazole ring.

A carboxyl group which may or may not be esterified or amidised is in particular the carboxyl group itself, or a carboxyl group esterified with a lower alkanol, or a carbamoyl group which is unsubstituted at the nitrogen atom or is monosubstituted or disubstituted at the nitrogen atom by alkyl, especially lower alkyl, aryl, in particular phenyl, or aralkyl, such as benzyl. The carbamoyl group can however also carry an alkylene radical, such as the tetramethylene or pentamethylene radical. The carbamoyl group $R_8$ can also be substituted at the nitrogen by the carbamoyl-methyl group.

Acyl is in particular an acyl radical of an organic acid, especially of an organic carboxylic acid. Thus, acyl is in particular alkanoyl, in particular having 2–18 carbon atoms, but especially lower alkanoyl, or is aroyl, such as naphthoyl-1, naphthoyl-2 and in particular benzoyl, or benzoyl or naphthoyl substituted by halogen, lower alkyl, lower alkoxy, trifluoromethyl, hydroxyl or lower alkanoyloxy, or is an acyl radical of an organic sulfonic acid, for example an alkanesulfonic acid, especially a lower alkanesulfonic acid, or of an arylsulfonic acid, especially of a phenylsulfonic acid which may or may not be lower alkyl-substituted or halogen-substituted, such as of benzenesulfonic acid or p-toluenesulfonic acid, or is carbamoyl, for example unsubstituted carbamoyl, lower alkyl-carbamoyl or aryl-carbamoyl, such as methyl-carbamoyl or phenyl-carbamoyl.

Esterified or etherified hydroxyl is, in particular, lower alkoxy or lower acyloxy, such as lower alkanoyloxy.

Esterified or etherified mercapto is in particular lower alkylmercapto or lower acylmercapto, such as lower alkanoylmercapto.

Acylated amino is in particular lower alkanoylamino or carbamoylamino.

In this description and the claims, the term "lower" used to qualify radicals and compounds denotes that these contain not more than 7, preferably not more than 4, carbon atoms.

In this specification, the general terms can have the following meaning:

Lower alkyl is, for example, n-propyl, n-butyl, isobutyl, sec.-butyl or tert.-butyl, as well as n-pentyl, n-hexyl, isohexyl or n-heptyl, and in particular methyl or ethyl. In aryl-lower alkyl, cycloalkyl-lower alkyl or heterocyclyl-lower alkyl, the lower alkyl radical is in particular methyl or ethyl, with the aryl, cycloalkyl or heterocyclyl radical having the above meaning.

Lower alkoxy is, for example, n-propoxy, n-butoxy, iso-butoxy, sec.-butoxy or tert.-butoxy and in particular methoxy or ethoxy.

Lower alkylmercapto is, for example, n-propyl-, n-butyl-, isobutyl-, sec.-butyl- or tert.-butyl-mercapto and in particular methylmercapto or ethylmercapto.

Lower alkylenedioxy is in particular methylenedioxy, ethylenedioxy or propylenedioxy.

Halogen can be fluorine or bromine but is preferably chlorine.

Lower alkanoyl is in particular propionyl or butyryl, but especially acetyl.

The novel compounds of the present invention can be in the form of mixtures of isomers or in the form of the pure isomers.

It is known that muramyl-peptides are good adjuvants which, when suitably mixed with antigens, can increase the immunogenicity of the latter. However, it has been found that they only show a short-lived activity, since they are relatively rapidly eliminated from the human or animal organism. In particular, it is only under certain conditions, which are unsuitable for clinical purposes, namely when mixed with antigens in an emulsion with mineral oil, that they are capable of inducing, in vivo, a cell-mediated immunity against soluble antigens. The novel compounds of the present invention now provide a marked potentiation of the immuno-response to the antigen, in particular also a cell-mediated immunity under clinically acceptable conditions of administration, as can be demonstrated with the experimental methods described below.

1. Potentiation of the cell-mediated immunity in vivo: increase in the delayed-type hypersensitivity to bovine serum albumin (BSA) and to sheep erythrocytes (SRBC) in guinea pigs Pirbright guinea pigs are immunised on day 0 with 1 mg of BSA or with 1 mg of SRBC—'ghosts' (SRBCG) in Freund's complete adjuvant by injection of 0.1 ml of an antigen-adjuvant mixture into each of the two hind paws. 3 weeks later, skin reactions are triggered by intracutaneous injection of 100 μg of BSA or 100 μg of SRBCG in 0.1 ml of buffered physiological salt solution and are quantified in terms of the reaction volume calculated 24 hours later from the erythema area and the increase in skin thickness. The antigen-specific increase in the reaction volume observed after 24 hours (delayed-type reaction) serves as a measure of cell-mediated immunity. BSA and SRBCG are too weak as immunogens to induce a delayed-type reaction by themselves or in a water-oil emulsion with Freund's incomplete adjuvant (10 parts of BSA solution or SRBCG suspension in 0.9% strength NaCl, mixed with 8.5 parts of Bayol F and 1.5 parts of Arlacel A); instead, for effective immunisation, they must be administered in complete adjuvant, added to the mycobacterium (5 mg of killed and lyophilised M. butyricum per 10 ml of Bayol F/Arlacel A).

In place of the mycobacteria, the novel compounds, containing either BSA (1 mg of BSA, 60 μg of MDP per animal) or SRBCG (1 mg of SRBCG, 25 μg of MDP per animal) as the antigen, were administered either as an antigen-oil mixture or as a suspension in carboxymethylcellulose (CMC). The novel compounds induce delayed-type reactions, in the absence of mycobacteria, with the experimental method which has been described.

A significant potentiation of the delayed-type reactivity of BSA and SRBCG can also be achieved by administering the novel compounds suspended in CMC, rather than incorporated into Freund's incomplete adjuvant. In this case, intramuscular administration has proved particularly effective. Under these circumstances, an equal amount of free muramyl-peptide, admixed to the CMC mixture, proved substantially less active than the new active substance. This demonstrates that under clinically acceptable conditions of administration, i.e. on administration with concomitant materials tolerated by the body, the novel compounds can induce cell-mediate immunity even against a soluble protein antigen.

2. Potentiation of the cell-mediate immunity in vivo: increase in the delayed-type hypersensitivity to BSA and to SRBCG in mice Male MAG mice are immunised on day 0 with graded doses of antigens (BSA-agarose or SRBCG) not conjugated with muramyl-peptide, or graded doses of antigens (BSA-agarose or SRBCG) conjugated with muramyl-peptide. The BSA-agarose preparations are administered subcutaneously in a dose of 0.1 to 100 $\mu$g (which in the case of the novel compounds with muramyl-peptides corresponds to a dose of active substance of 0.0029–6 $\mu$g per animal) in a volume of 0.2 ml of buffered physiological sodium chloride solution. The SRBCG preparations are administered in a dose of 0.01–3 mg (which in the case of the novel compounds with muramyl-peptides corresponds to a dose of active substance of 0.25–75 $\mu$g per animal) intraperitoneally in a volume of 0.5 ml in buffered physiological salt solution, or intradermally, or divided over 3 paws, in a volume of 0.05 ml.

4 to 20 days later, delayed-type reactions are triggered by injecting 100 $\mu$g of BSA or $10^8$ SRBC in 20 $\mu$l of buffered physiological salt solution into the left hind paw, and the reactions are quantified in terms of the reaction volume determined from the swelling of the paw 24 and 48 hours later. The observed antigen-specific increase in the volume of the paw serves as a measure of the cell-mediated immunity.

Starting from day 14 after immunisation with BSA-agarose-MDP compounds, pronounced delayed-type reactions occur even at a very low dosage (0.1 $\mu$g, corresponding to 0.006 $\mu$g of active substance). In contrast, free BSA-agarose is incapable of causing sensitisation for delayed-type reactions. Equally, SRBCG-MDP compounds, in particular after intradermal administration, are capable of inducing delayed-type reactivity, which is significantly more pronounced than the reactivity which is attainable after sensitisation with SRBCG which is not bonded to muramyl-peptide.

This again shows that the novel compounds can substantially increase cellular immunity.

3. Potentiation of humoral immunity in vivo: increase in antibody production against BSA in mice NMRI mice are immunised on day 0 by intraperitoneal injection of 0.1 to 100 $\mu$g of BSA bonded to muramyl-peptides (0.0014 to 6.0 $\mu$g of active substance). 10, 17 and 28 days later, serum samples are taken and examined for their content of anti-BSA antibodies by means of a passive haemagglutination technique. At the dose used, free BSA is sub-immunogenic for the receptor animals, i.e. it can only trigger a very slight production of antibodies, if any. The bonding of BSA to a muramyl-peptide permits a 2–3-fold increase in the antibody titre in the serum (titre-sum of the $\log_2$ titre differences on three blood-sampling days). It is furthermore noteworthy that the novel compounds, which in addition have been coupled to agarose as a carrier, are even more strongly immunogenic after intraperitoneal or subcutaneous administration.

The experiments described show that the novel compounds according to the invention can also substantially increase humoral immunity.

The new antigen derivatives are novel or improved known vaccines and are used for novel inoculation methods or for the simplification of conventional inoculation methods (for example by making it possible to reduce the number of inoculations required to maintain protection over prolonged periods).

The invention in particular relates to novel antigen derivatives which contain antigens, as ingredients of vaccines against parasites, bacteria, viruses, tumour cells or physiological body-innate constituents, their modified forms or sub-units thereof, covalently bonded, directly or via spacers, to muramyl-peptides of the formula II, in which $R_1$, $R_3$, $R_4$, $R_6$ and $R_7$ are hydrogen, X is carbonyl and $R_2$ is lower alkyl which is unsubstituted or substituted by hydroxyl or lower alkoxy, or is phenyl which is unsubstituted or substituted by hydroxyl, lower alkoxy, lower alkyl or halogen, and $R_8$, $R_9$, $R_{10}$, $R_{11}$, $R_{12}$ and $R_{13}$ are as defined above.

The invention especially relates to novel antigen derivatives which contain antigens as ingredients of vaccines against parasites, bacteria, viruses, tumour cells or physiological body-innate constituents, their modified forms or sub-units thereof, covalently bonded, directly or via spacers, to muramyl-peptides of the formula II, in which $R_1$, $R_4$, $R_6$ and $R_7$ are hydrogen, X is carbonyl, $R_2$ is lower alkyl which is unsubstituted or substituted by hydroxyl or lower alkoxy or is phenyl which is unsubstituted or substituted by hydroxyl, lower alkoxy, lower alkyl or halogen, $R_3$ is methyl and $R_8$, $R_9$, $R_{10}$, $R_{11}$, $R_{12}$ and $R_{13}$ are as defined above.

More especially, the invention relates to novel antigen derivatives which contain antigens as ingredients of vaccines against parasites, bacteria, viruses, tumour cells or physiological body-innate constituents, their modified forms or sub-units thereof, covalently bonded, directly or via spacers, to muramyl-peptides of the formula II, in which $R_1$, $R_4$, $R_6$ and $R_{13}$ are hydrogen, X is carbonyl, $R_2$ is lower alkyl which is unsubstituted or substituted by hydroxyl or methoxy or is phenyl which is unsubstituted or substituted by hydroxyl, methoxy, methyl, ethyl or halogen, $R_3$ is hydrogen or methyl, $R_7$ and $R_9$ are hydrogen, $R_8$ is lower alkyl, lower alkylmercapto-lower alkyl, hydroxy-lower alkyl, benzyl, p-hydroxybenzyl or phenyl and $R_{10}$, $R_{11}$ and $R_{12}$ are carboxyl, carbo-lower alkoxy or carbamoyl and $R_{11}$ can also be hydrogen.

More especially still, the invention relates to novel antigen derivatives which contain antigens as ingredients of vaccines against parasites, bacteria, viruses, tumour cells or physiological body-innate constituents, their modified forms or sub-units thereof, covalently bonded, directly or via spacers, to muramyl-peptides of the formula II, in which $R_1$, $R_4$, $R_6$ and $R_{13}$ are hydrogen, X is carbonyl, $R_2$ is lower alkyl which is unsubstituted or substituted by hydroxyl or methoxy or is phenyl which is unsubstituted or substituted by hydroxyl, methoxy, methyl, ethyl or halogen, $R_3$ and $R_9$ are hydrogen or methyl, $R_8$ is methyl, ethyl, n-propyl, i-propyl, 2-methylpropyl, methylmercaptomethyl, hydroxymethyl, hydroxyethyl, phenyl, benzyl or p-hydroxybenzyl and $R_{10}$, $R_{11}$ and $R_{12}$ are carboxyl, carboxy-lower alkyl or carbamoyl, and $R_{11}$ can also be hydrogen.

The invention also relates to novel antigen derivatives which contain antigens as ingredients of vaccines against bacteria, viruses, tumour cells or physiological body-innate constituents, their modified forms or sub-units thereof, covalently bonded, directly or via spacers, to muramyl-peptides of the formula II, in which $R_1$, $R_4$, $R_6$ and $R_{13}$ are hydrogen, X is carbonyl, $R_7$ and $R_8$ together are propylene or butylene and $R_2$, $R_3$, $R_9$, $R_{10}$, $R_{11}$ and $R_{12}$ are as defined above.

Spacers in the above definitions are in particular $\alpha,\omega$-diamino-lower alkanes, lower alkyl-dicarboxylic acids and natural $\alpha$-amino-lower alkanecarboxylic acids.

In particular, the invention relates to the novel antigen derivatives described in the examples.

The novel compounds may be prepared by methods known per se.

Thus, they may be obtained if an antigen, which may or may not be linked to spacers, is condensed with muramyl-peptides, which may or may not be linked to spacers, one of the two moieties possessing free amino, hydroxyl or mercapto groups and the other possessing carboxylic acid groups, and, if desired, the resulting compound is condensed onto a carrier which may or may not be linked to spacers.

The condensations are carried out, for example, by reacting one of the compounds, in the form of an activated carboxylic acid, with the other compound, in the form of the free amino, hydroxyl or mercapto compound. The activated carboxyl group can, for example, be an acid anhydride but preferably an acid azide, an acid amide, such as an imidazolide or isoxazolide or an activated ester. Specific examples of activated esters are the cyanomethyl ester, carboxymethyl ester, p-nitrophenylthio ester, methoxyethylthio ester, acetylaminoethylthio ester, p-nitrophenyl ester, 2,4,5-trichlorophenyl ester, N-hydroxysuccinimide ester, N-hydroxyphthalimide ester, 8-hydroxyquinoline ester and N-hydroxypiperidine ester. Active esters can also, if desired, be obtained with a carbodiimide in the presence of N-hydroxysuccinimide, or with an unsubstituted or, for example, halogen-, methyl- or methoxy-substituted, 1-hydroxybenzotriazole or 3-hydroxy-4-oxo-3,4-dihydro-benzo[d]-1,2,3-triazine.

The leaving groups used in this condensation must be non-toxic or must be easily removable to avoid the compounds, which are in most cases of high molecular weight, retaining toxic fragments by adsorption.

Preferred active esters are therefore those with N-hydroxysuccinimide or their C-substitution products, such as N-hydroxy-methylsuccinimide or N-hydroxy-dimethylsuccinimide; alternatively, the reaction with a carbodiimide, such as carbodiimide itself or 1-ethyl-3-(3-dimethylaminopropyl)-carbodiimide is preferred.

The above reactions are carried out in the usual manner in the presence or absence of diluents, condensation agents and/or catalytic agents, if necessary at a lowered or elevated temperature. Preferably, in order not to destroy the antigens, the reactions are carried out in an aqueous medium and in a pH range of 6–9, in particular 7–8.

The invention also relates to those embodiments of the process in which a compound obtainable as an intermediate at any stage is used as the starting material and the missing steps are carried out, or in which a starting material is formed under the reaction conditions, or in which a reactant is, where appropriate, employed in the form of a derivative, such as a salt, and/or in the form of an isomer mixture or of the pure isomer.

The starting materials used for carrying out the condensations according to the invention are preferably those which result in the groups of end products particularly mentioned at the outset and especially those which result in the end products which have been specifically described or singled out.

The starting materials used are known or, where they are new, can be prepared by methods known per se.

The present invention also relates to pharmaceutical preparations which contain the novel antigen derivatives. The pharmaceutical preparations according to the invention are those intended for enteral, such as oral or rectal, or parenteral administration to warm-blooded animals and which contain the pharmacological active substance as the sole ingredient or together with a pharmaceutically acceptable carrier.

The novel pharmaceutical preparations contain from about 10% to about 95%, preferably from about 20% to about 90% of the active substance. Pharmaceutical preparations according to the invention can be in dosage unit form, such as coated tablets, tablets, capsules, suppositories or ampoules.

The pharmaceutical preparations of the present invention are prepared in a manner known per se, for example by means of conventional mixing, granulating, coating, dissolving or lyophilising methods. For example, pharmaceutical preparations for oral use can be obtained by combining the active substance with solid excipients, granulating the resulting mixture, if desired, and converting the mixture or granules, if desired or required after addition of suitable adjuncts, to tablets or to cores for sugar-coated tablets.

Suitable excipients are, in particular, fillers, such as sugar, for example lactose, sucrose, mannitol or sorbitol, cellulose preparations and/or calcium phosphates, e.g. tricalcium phosphate or calcium hydrogen phosphate, also binders, such as starch pastes, obtained using, for example, corn starch, wheat starch, rice starch or potato starch, gelatin, tragacanth, methylcellulose, hydroxypropylmethylcellulose, sodium carboxymethylcellulose and/or polyvinylpyrrolidone, and/or, if desired, disintegrators, such as the above starches, also carboxymethyl-starch, crosslinked polyvinylpyrrolidone, agar, alginic acid or a salt thereof, such as sodium alginate. Adjuncts are chiefly glidants and lubricants, for example silicic acid, talc, stearic acid or salts thereof, such as magnesium stearate or calcium stearate, and/or polyethylene glycol. Cores for sugar-coated tablets are provided with suitable coatings, which may be resistant to gastric juices, using, inter alia, concentrated sugar solutions, which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or the sugar coatings, for example to identify or indicate different active ingredients.

Further pharmaceutical preparations which can be used orally are dry-filled capsules made from gelatin, as well as soft sealed capsules made from gelatin and a plasticiser, such as glycerol or sorbitol. The dry-filled capsules can contain the active ingredient in the form of granules, for example in admixture with fillers such as lactose, binders, such as starches, and/or glidants, such as talc or magnesium stearate, with or without the presence of stabilisers. In soft capsules, the active ingredient is preferably dissolved or suspended in suitable liquids, such as fatty oils, paraffin oil or liquid polyethylene glycols, to which, again, stabilisers can be added.

Suitable compositions for parenteral administration are in particular aqueous solutions of an active ingredient in a water-soluble form, for example the form of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions which contain viscosity-increasing materials, for example sodium carboxymethylcellulose, sorbitol and/or dextran, with or without stabilisers.

A preferred composition for administration comprises a solution or suspension of the novel antigen derivatives, preferably containing up to 10 percent by weight of carboxymethylcellulose.

The invention also relates to the use of the novel antigen derivatives as pharmacologically active substances, especially as immunising agents, preferably in the form of pharmaceutical preparations. The dosage of the active substance depends on the species of the warm-blooded animal, the body weight, the age and the individual condition, as well as the mode of administration.

By analogy with the dosages recognised and known in the known methods of inoculation, the novel vaccines are administered in weight units or international units; for example, antigen derivatives containing lymphoblasts are given 1–6 times, at intervals of 2 to 8 weeks, in an amount such that each injection contains $10^6$–$10^{10}$ cell organisms. Preferably, the preparations should contain 5–200 micro-g of muramyl-peptides per mg of protein.

Preferably, for immunisation with soluble compounds, the corresponding amount of antigen derivative is employed in a Falz solution (BSS) consisting of 0.14 g of calcium chloride, 8.0 g of sodium chloride, 0.2 g of magnesium sulfate $0.7H_2O$, 0.2 g of magnesium chloride $0.6H_2O$, 0.6 g of potassium dihydrogen phosphate and 0.24 g of disodium hydrogen phosphate $0.2H_2O$ per liter of water. If a depot effect is desired (for example in the case of local, intradermal or intramolecular administration) carboxymethylcellulose (final concentration preferably 5%) can be added to the dissolved antigen derivative.

Insoluble macromolecular antigen derivatives are preferably administered as a suspension in BSS and carboxymethylcellulose as the stabiliser (final concentration preferably 5%). To prepare a stable suspension the mixture, cooled in ice, is preferably treated in concentrated form with ultrasonic vibrations.

Antigen derivatives with cells are in particular administered in a tissue culture medium especially suitable for the particular type of cell (for example EAGLE's high aminoacid medium for lymphocytes) [cf. Click et al., Cell. Immunol., vol 3, p. 264–276 (1972)].

The invention also relates to the novel muramylpeptides of the formula II, to be used as starting materials, in which X is a carbonyl group, $R_1$ is hydrogen, alkyl, unsubstituted or substituted benzyl or acyl, $R_2$ is unsubstituted or substituted alkyl or carbocyclic aryl, $R_4$ and $R_6$ independently of one another are hydrogen, alkyl, unsubstituted or substituted benzyl or acyl, $R_3$ is hydrogen or alkyl, at least one of the radicals $R_7$, $R_9$ and $R_{13}$ is lower alkyl, especially methyl, and the others are hydrogen, $R_8$ is hydrogen, lower alkyl, free, esterified or etherified hydroxy-lower alkyl, free, esterified or etherified mercapto-lower alkyl, free or acylated amino-lower alkyl, cycloalkyl having 5 or 6 carbon atoms, cycloalkyl-lower alkyl, in which the cycloalkyl radical contains 5 or 6 carbon atoms, unsubstituted or substituted aryl or aralkyl, or nitrogen-containing heterocyclyl or heterocyclyl-lower alkyl, $R_7$ and $R_8$ together can also be alkylene having 3 or 4 carbon atoms, and the radicals $R_{10}$, $R_{11}$ and $R_{12}$ independently of one another are a carboxyl radical which may or may not be esterified or amidised, and $R_{11}$ can also be hydrogen.

These compounds are obtained when, in a manner known per se, a compound of the formula

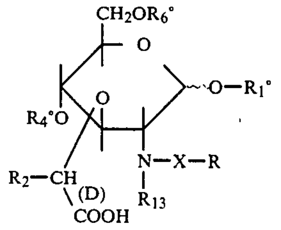

(IV)

in which X, R, $R_2$ and $R_{13}$ are as defined above and $R_1^o$, $R_4^o$ and $R_6^o$ are, respectively, the radicals $R_1$, $R_4$ and $R_6$ or are easily detachable protective groups, or a derivative thereof, is condensed with a compound of the formula

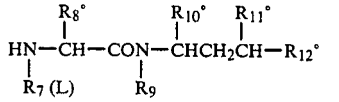

(V)

in which $R_8^o$, $R_{10}^o$, $R_{11}^o$ and $R_{12}^o$ are as defined for $R_8$, $R_{10}$, $R_{11}$ and $R_{12}$, with the proviso that carboxyl groups present in these radicals and, if desired, free hydroxyl groups present in these radicals, are protected by easily detachable protective groups, any protective groups present subsequently being detached.

The condensation is carried out, for example, by reacting the compound IV, in the form of the activated carboxylic acid, with the amino compound V, or by reacting the acid IV with the compound V, in which the amino group is in an activated form. The activated carboxyl group can for example be an acid anhydride, preferably a mixed acid anhydride such as an acid azide, an acid amide, such as an imidazolide or isoxazolide, or an activated ester. Specific examples of activated esters are the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, 2-hydroxy-1,2-dihydro-1-carboethoxy-quinoline ester, N-hydroxypiperidine ester or enol esters obtained from N-ethyl-5-phenyl-isoxaolium-3'-sulfonate. Activated esters can also, if desired, be obtained with a carbodiimide, in the presence of N-hydroxysuccinimide, or with an unsubstituted or, for example, halogen-, methyl- or methoxy-substituted 1-hydroxybenzotriazole, or 3-hydroxy-4-oxo-3,4-dihydro-benzo[d]-1,2,3-triazine.

The amino group is, for example, activated by reaction with a phosphite-amide.

Preferred methods of reaction with activated esters are those with N-ethyl-5-phenyl-isoxazolium-3'-sulfonate (Woodward reagent K) or 2-ethoxy-1,2-dihydro-1-carboethoxy-quinoline or carbodiimide.

Easily detachable protective groups are those which are known from peptide chemistry or sugar chemistry. Preferred protective groups for carboxyl groups are tertiary butyl, benzyl or benzhydryl, and preferred protective groups for hydroxyl groups are acyl radicals, for example lower alkanoyl radicals, such as acetyl, aroyl radicals, such as benzoyl and especially radicals derived from carbonic acid, such as benzyloxycarbonyl or lower alkoxycarbonyl, or alkyl, especially tert.butyl, unsubstituted or nitro-, lower alkoxy- or halogen-substituted benzyl or tetrahydropyranyl or unsubstituted or substituted alkylidene radicals which join the oxygen atoms in the 3-position and 6-position. Such alkylidene radicals are, in particular, a lower alkylidene radical, especially the ethylidene, isopropylidene or propylidene radical, or an unsubstituted or substituted, preferably p-substituted, benzylidene radical.

These protective groups can be detached by methods known per se. Thus, they can be removed hydrogenolytically, for example with hydrogen in the presence of a noble metal catalyst, such as a palladium or platinum catalyst, or by acid hydrolysis.

The starting materials used are known or can be prepared by methods known per se.

An alternative method of preparation of these novel starting materials comprises condensing, in a manner known per se, a compound of the formula VI

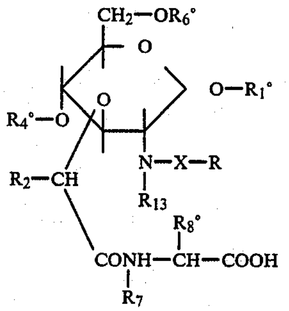
(VI)

in which R, $R_1^o$, $R_2$, $R_4^o$, $R_6^o$, $R_7$ and $R_8^o$ are as defined above, with a compound of the formula

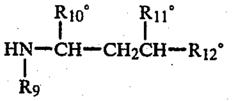
(VII)

in which $R_{10}^o$, $R_{11}^o$ and $R_{12}^o$ are as defined above, with the proviso that carboxyl groups and, if desired, free hydroxyl groups present in the radicals $R_8^o$, $R_{10}^o$, $R_{11}^o$ and $R_{12}^o$ are protected by easily detachable protective groups, and after condensation detaching any protective groups present.

The condensation is carried out, for example, by reacting the compound VI, in the form of the activated carboxylic acid, with the amino compound VII, or reacting the acid VI with the compound VII, wherein the amino groups are in an activated form. The activated carboxyl group can, for example, be an acid anhydride, preferably a mixed acid anhydride, an acid amide or an activated ester. Particular examples are the above acid anhydrides, amides or esters. The amino group is activated, for example, by reaction with a phosphiteamide.

The easily detachable protective groups, in turn, correspond to those already mentioned above. They can be detached by methods known per se, e.g. hydrogenolytically, for example with hydrogen in the presence of a nobel metal catalyst, such as a palladium or platinum catalyst, or by acid hydrolysis.

The starting materials can be obtained in a manner known per se. For example, corresponding sugars unsubstituted in the 3-position can be reacted with a halogeno-$R_2$-acetamido-$R_7^o$-acetic acid, or a compound of the formula III can be reacted, in the manner indicated above, with an amino-$R_7$-acetic acid wherein the carboxyl group is protected, after which reaction the protective group is detached.

A further method for introducing the side chain present in the 3-position of the sugar residue comprises reacting a compound

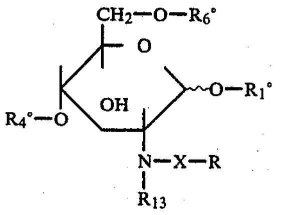
(VIII)

in which X, R, $R_1^o$, $R_4^o$, $R_6^o$ and $R_{13}$ are as defined above, and any hydroxyl groups which may be present are protected with an easily detachable protective group, with a compound of the formula

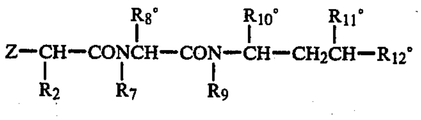
(IX)

in which Z is a reactive esterified hydroxyl group and $R_8^o$, $R_{10}^o$, $R_{11}^o$ and $R_{12}^o$ are as defined above, and detaching any protective groups which may be present.

A reactive esterified hydroxyl group is in particular a hydroxyl group esterified with a strong inorganic or organic acid, especially with a hydrohalic acid, such as hydrochloric acid, hydrobromic acid or hydriodic acid.

The easily detachable protective groups correspond to those already mentioned above. They can be detached by methods known per se, e.g. hydrogenolytically, for example with hydrogen in the presence of a noble metal catalyst, such as a palladium or platinum catalyst, or by acid hydrolysis.

The invention also relates to the novel muramylpeptides, to be used as starting materials, of the formula II, in which X is a carbonyl group, $R_1$, $R_4$ and $R_6$ are tri-lower alkylsilyl, especially trimethylsilyl, $R_2$ is unsubstituted or substituted alkyl or carbocyclic aryl, $R_3$ is hydrogen or alkyl, $R_7$ and $R_{13}$ are hydrogen or lower alkyl, $R_8$ is hydrogen, lower alkyl, free, esterified or etherified hydroxy-lower alkyl, free, esterified or etherified mercapto-lower alkyl, free or acylated amino-lower alkyl, cycloalkyl having 5 or 6 carbon atoms, cycloalkyl-lower alkyl, in which the cycloalkyl radical contains 5 or 6 carbon atoms, unsubstituted or substituted aryl or aralkyl or nitrogen-containing heterocyclyl or heterocyclyl-lower alkyl, $R_7$ and $R_8$ together can also be alkylene having 3 or 4 carbon atoms, $R_9$ is hydrogen or lower alkyl and the radicals $R_{10}$, $R_{11}$ and $R_{12}$ independently of one another are a carboxyl radical which may or may not be esterified or amidised, and $R_{11}$ can also be hydrogen.

These compounds can be obtained if a compound of the formula

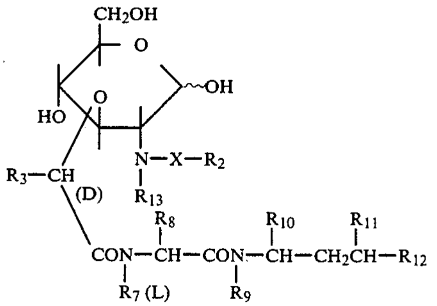

(XI)

is reacted, in a manner known per se, with a reactive ester of a tri-lower alkylsilyl compound.

Preferred reactive esters of a tri-lower alkylsilyl compound are tri-lower alkylsilyl halides, especially chlorides or bromides, bis-lower alkyl-silyl-acetamide or bis-lower alkyl-silyl-sulfamide.

The reaction is preferably carried out in a solvent which does not contain any reactive hydroxyl or amino group, such as dimethylformamide, dioxane, tetrahydrofurane, dimethoxyethane or chloroform.

The following examples illustrate the present invention without in any way restricting the scope thereof. Temperatures are given in degrees Centigrade.

EXAMPLE 1

500 mg of 2-acetamido-3-O-{[L-1-(D-1-carbamoyl-3-succinimido-oxycarbonyl-propyl)-carbamoyl-ethyl]-carbamoylmethyl}-2-deoxy-D-glucose are added, with stirring, to a solution of 1 g of bovine serum albumin in 100 ml of an 0.1M sodium bicarbonate/0.5M sodium chloride solution. The resulting solution is stirred for 4 hours at room temperature and is then sterile-filtered (MF-Millipore, 0.45 μm filter). The conjugated bovine serum albumin is separated from low molecular weight reaction products and from salts by the dial-filtration process through an Amikon UM-10 filter, and is freeze-dried.

The quantitative determination of the muramylpeptide bound to the bovine serum albumin is carried out by means of the Morgan-Elson reaction in the modified version of J. M. Ghuysen et al. [in "Methods in Enzymology" 8, (1966) 629]. On average, 60 μg of the muramylpeptide are found in 1 mg of bovine serum albumin compound.

The succinimido-ester used as the starting material can for example be prepared as follows:

1 mmol of 2-acetamido-3-O-{[L-1-(D-1-carbamoyl-3-carboxy-propyl)-carbamoyl-ethyl]-carbamoyl-methyl}-2-deoxy-D-glucose, 1 mmol of dicyclohexylcarbodiimide and 1.1 mmols of N-hydroxysuccinimide are dissolved in 3 ml of absolute dimethylformamide and the mixture is stirred for 20 hours in a closed vessel, with exclusion of moisture. The dicyclohexylurea which has precipitated is separated off, the solvent is evaporated off in a high vacuum and the residue is treated with ether and then filtered off with suction and dried. The succinimido-oxyester thus obtained can be stored in the absence of moisture, for example in a nitrogen ampoule.

EXAMPLE 2

Condensation of the antigen derivative, obtained in Example 1, with activated agarose, using a commercially available agarose derivative from BIO-RAD, namely Affi-Gel 10, which contains, on an agarose skeleton, ether side chains ("spacer arms") of N-alkyl-succinamides which are esterified with N-hydroxysuccinimide.

120 mg of the bovine serum albumin derivative obtained according to Example 1 are dissolved in 12.5 ml of 0.1M phosphate buffer of pH 7.3 at 4° C. 500 mg of Affi-Gel 10 are then suspended in the solution by shaking, and shaking is continued for 4 hours at 4° C. The active ester groups which still remain are reacted by 30 minutes' treatment with a 1M ethanolamine.HCl/0.1M phosphate buffer solution (pH 7.3). Thereafter, the gel is packed into a column and is washed first with 200 ml of 0.1M phosphate buffer/1M sodium chloride solution (pH 7.3) and then with 20 ml of physiological sodium chloride solution.

The determination of bovine serum albumin/-muramylpeptide compounds condensed onto the Affi-Gel 10 is carried out by quantitative analysis of representative bovine serum albumin aminoacids in the total hydrolysates of defined aliquot portions of gel. On average, 9–10 mg of the bovine serum albumin/muramylpeptide derivative are bound to 1 ml of swollen Affi-Gel 10.

EXAMPLE 3

Ovine erythrocyte membranes are isolated from fresh ovine blood by the method of J. I. Dodge et al. [Arch. Biochem. Biophys. 100. (1963) p. 114–180]. 400 mg of 2-acetamido-3-O-{[L-1-(D-1-carbamoyl-3-succinimido-oxycarbonyl-propyl)-carbamoyl-ethyl]-carbamoyl-methyl}-2-deoxy-D-glucose are added, with stirring, to a suspension of 500 mg of ovine erythrocyte membranes in 50 ml of 0.1M sodium bicarbonate/0.1M sodium chloride solution, and the mixture is then stirred for 4 hours at room temperature. Thereafter, the erythrocyte membrane conjugate is sedimented by ultracentrifuging for one hour at 90,000 g and 4° C. The sediment is washed three times with phosphate-buffered sodium chloride solution (in each case by resuspending and ultracentrifuging) and once with distilled water. The washed erythrocyte membrane conjugate is suspended in 100 ml of distilled water and freeze-dried.

The quantitative determination of muramyl-dipeptide bound to the ovine erythrocytes is carried out by means of the Morgan-Elson reaction and indicates 25 μg of muramyl-dipeptide per mg of erythrocyte membrane.

EXAMPLE 4

100 mg of group C polysaccharide of Neisseria meningitidis and 110 mg (0.2 mmol) of 2-acetamido-3-O-{L-1-(D-1-carbamoyl-3-N-aminoethyl-carbamoyl-propyl)-carbamoyl-ethyl]-carbamoyl-methyl}-2-deoxy-D-glucose-HCl are dissolved in 10 ml of distilled water and the pH value of the solution is brought to 5 with dilute hydrochloric acid.

19.2 mg of 1-ethyl-3-(3-dimethylaminopropyl)-carbodiimide.HCl are added, with stirring, to the solution. The mixture is stirred for 1 hour at room temperature, the pH value being kept at 5 by addition of dilute sodium hydroxide solution, 5 ml of 2M sodium acetate buffer solution of pH 5 are then added, and stirring is continued for a further 30 minutes. The pH value is then brought to 7 with sodium hydroxide solution. The solution is sterile-filtered, dialysed against distilled water at 4° C., and then freeze-dried.

The quantitative determination of desmethyl-muramyldipeptide coupled to the C-polysaccharide is carried out as described in Example 1, using the Morgan-Elson reaction, and indicates 80 μg of desmethyl-muramyl-dipeptide per mg of polysaccharide.

The 2-acetamino-3-O-{[L-1-(D-1-carbamoyl-3-N-aminoethyl-carbamoyl-propyl)-carbamoyl-ethyl]-methyl}-2-deoxy-D-glucose hydrochloride used can be prepared, for example, as follows:

1 mmol of 2-acetamino-3-O-{[L-1-(D-1-carbamoyl-3-carboxy-propyl)-carbamoyl-ethyl]-carbamoyl-methyl}-2-deoxy-D-glucose and 2 mmols of N-ethyl-N'-(3-dimethylaminopropyl)-carbodiimide.HCl are dissolved in 10 ml of water and the pH is brought to 5.0 with hydrochloric acid; a solution of 5 mmols of ethylenediamine dihydrochloride in 10 ml of water is then added. The batch is stirred at pH 5.0 and room temperature for 6 hours. The mixture is applied to a weakly acidic cation exchanger column of Amberlite CG 50 II, column size 2.5×45 cm, and elution is carried out with a linear gradient from 0.05M pyridine acetate, pH 6 (300 ml) to 0.5M pyridine acetate, pH 3.7 (300 ml). The fractions which contain the resulting 2-acetamino-3-O-{[L-1-(D-1-carbamoyl-3N-aminoethyl-carbamoyl-propyl)-carbamoylethyl]-carbamoyl-methyl}-2-deoxy-D-glucose acetate (the fractions are tested, and characterised, by means of ninhydrin and high voltage electrophoresis) are freeze-dried. The conversion to the hydrochloride form is carried out as follows. The lyophilisate is dissolved in 6 ml of 0.2N HCl and chromatographed on a Bio-Gel P2 column, size 2.5×90 cm, with water as the eluent. The fractions containing 2-acetamino-3-O-{[L-1-(D-1-carbamoyl-3-N-aminoethyl-carbamoyl-propyl)-carbamoylethyl]-carbamoyl-methyl}-2-deoxy-D-glucose hydrochloride are freeze-dried. The preparation is a single compound according to high voltage electrophoresis. On determining the constituents in total hydrolysates, the molecular ratio of 1 muramic acid: 1 L-alanine: 1 D-glutamic acid: 1 ethylenediamine is found.

Analogously, starting from the corresponding muramyl-dipeptides, the following β'-aminoethylamide.HCl compounds are obtained: 2-acetamino-3-O-{D-1-[L-1-(D-1-carbamoyl-3-N-aminoethyl-carbamoyl-propyl)-carbamoylethyl]-carbamoyl-ethyl}-2-deoxy-D-glucose.HCl, 2-benzoylamino-3-O-{D-1-[L-1-(D-1-carbamoyl-3-N-aminoethyl-carbamoyl-propyl)-carbamoyl-ethyl]-carbamoyl-ethyl}-2-deoxy-D-glucose.HCl, 2-benzoylamino-3-O-{[L-1-(D-1-carbamoyl-3-N-aminoethyl-carbamoyl-propyl)-carbamoyl-ethyl]-carbamoyl-methyl}-2-deoxy-D-glucose.HCl, 2-acetamino-3-O-{[L-1-(D-1-N-carbamoyl-methyl-carbamoyl-3-N-aminoethyl-carbamoylpropyl)-carbamoyl-ethyl]-carbamoyl-methyl}-2-deoxy-D-glucose.HCl, 2-benzoylamino-3-O-{[L-1-(D-1-carbamoyl-3-N-aminoethyl-carbamoyl-propyl)-carbamoyl-propyl]-carbamoylmethyl}-2-deoxy-D-glucose.HCl, 2-propionylamino-3-O-{[L-1-(D-1-carbamoyl-3-N-aminoethyl-carbamoyl-propyl)-carbamoyl-ethyl]-carbamoyl-methyl}-2-deoxy-D-glucose.HCl, 2-acetylamino-3-O-{[L-1-(D-1-carbamoyl-3-N-aminoethyl-carbamoyl-propyl)-carbamoyl-propyl]-carbamoyl-methyl}-2-deoxy-D-glucose.HCl, 2-acetylamino-3-O-{[L-1-(D-1-carbamoyl-3-N-aminoethyl-carbamoyl-propyl)-carbamoyl-2-hydroxyethyl]-carbamoyl-methyl}-2-deoxy-D-glucose.HCl, 2-propionylamino-3-O-{[L-1-(D-1- (or 3)-carboxy-3 (or 1)-N-aminoethyl-carbamoyl-propyl)-carbamoyl-ethyl]-carbamoylmethyl}-2-deoxy-D-glucose.HCl, 2-benzoylamino-3-O-{[L-1-(D-1-N-carbamoyl-methyl-carbamoyl-3-N-aminoethyl-carbamoylpropyl)-carbamoyl-ethyl]-carbamoyl-methyl}-2-deoxy-D-glucose.HCl, 2-benzoylamino-3-O-{L-1-(D-1-carboxy-3-N-aminoethyl-carbamoyl-propyl)-carbamoyl-ethyl)-carbamoylmethyl}-2-deoxy-D-glucose.HCl, 2-acetamino-3-O-{[L-1-(D-1-carbamoyl-3-N-aminoethyl-carbamoyl-propyl)-carbamoyl-2'-methyl-propyl]-carbamoyl-methyl}-2-deoxy-D-glucose. HCL, 2-acetamino-3-O-{D-1-[L-1-(D-1-carbamoyl-3-(1-N-aminoethyl-carbamoyl)-ethyl-carbamoyl-propyl)-carbamoylethyl]-carbamoyl-ethyl}-2-deoxy-D-glucose.HCl, 2-acetamino-3-O-{[L-1-(D-1-carboxy-3-N-aminoethyl-carbamoylpropyl)-carbamoyl-2'-methyl-propyl]-carbamoyl-methyl}-2-deoxy-D-glucose.HCl, 2-acetamino-3-O-{[L-1-(D-1-carbamoyl-3-N-aminoethyl-carbamoyl-propyl)-carbamoyl-N,N-tetramethylene]-carbamoyl-methyl}-2-deoxy-D-glucose.HCl, 2-acetamino-3-O-{[L-1-(D-1-carbamoyl-3-N-aminoethylcarbamoyl-propyl)-carbamoyl-ethyl]-N-methyl-carbamoylmethyl}-2-deoxy-D-glucose.HCl or 2-benzoylamino-3-O-{[L-1-(D-1-carbamoyl-3-N-aminoethyl-carbamoyl-propyl)-carbamoyl-2'-methyl-propyl]-carbamoyl-methyl}-2-deoxy-D-glucose.HCl.

These compounds are condensed with group C-polysaccharide of Neisseria meningitidis, as described above.

EXAMPLE 5

Immediately after isolation, merozoites of the malaria pathogen Plasmodium knowlesi—the entire yield from the blood of one infected Rhesus monkey [for the method of isolation of merozoites, cf. G. H. Mitchel et al. (1975), Immunology, 29, 397]-are suspended in a solution of 100 mg (0.17 mmol) of 2-acetamino-3-O-{[L-1-(D-1-carbamoyl-3-succinimido-oxycarbonyl-propyl)-carbamoylethyl]-carbamoyl-methyl}-2-deoxy-D-glucose in 15 ml of physiological buffer solution of pH 7.2. The suspension is incubated for one hour at 37° C. The conjugates are then sedimented by centrifuging. The sediment is washed by resuspending it in physiological buffer solution and again centrifuging. The washed merozoite conjugates are suspended in 10% autologous Rhesus monkey serum and freeze-dried, by the method of G. H. Mitchel (loc. cit.).

The quantitative determination of muramyl-dipeptide coupled to the merozoites is carried out by means of the Morgan-Elson reaction and indicates 40–60 μg of muramyl-dipeptide per mg of merozoites.

EXAMPLE 6

$10^9$ T-lymphoblasts of CBA/J mice are suspended in a solution of 200 mg (0.34 mmol) of 2-acetamino-3-O-{[L-1-(D-1-carbamoyl-3-succinimido-oxycarbonyl-propyl)-carbamoylethyl]-carbamoyl-methyl}-2-deoxy-D-glucose in 20 ml of phosphate-buffered physiological sodium chloride solution of pH 7.2. (The T-lymphoblasts are obtained in a "mixed lymphocyte culture" against C57BL/6 mouse stimulator cells by the method of L. C. Anderson et al., The Journal of Experimental Medicine, 146 (1977), 1124). The suspension is incubated for 90 minutes at room temperature. The lymphoblast conjugates are then sedimented by centrifuging and washed by resuspending in phosphate-buffered physiological sodium chloride solution and again centrifuging.

The quantitative determination of muramyl-dipeptide coupled to the T-lymphoblasts is carried out by means of the Morgan-Elson reaction (see Example 1) and indicates 60–70 μg of muramyl-dipeptide per $10^7$ T-lymphoblasts.

EXAMPLE 7

Bovine serum albumin coupled to the compounds shown below is obtained analogously to the preceding examples: 2-acetamido-3-O-{D-1[L-1-[D-1-carbamoyl-3-carboxy-propyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoyl-ethyl]-carbamoyl-ethyl}-2-deoxy-α,β-D-glucose, 2-benzoylamino-3-O-{[L-1-(D-1-carbamoyl-3-carboxy-propyl)-carbamoyl-ethyl]-carbamoyl-methyl}-2-deoxy-α,β-D-glucose, 2-acetamido-3-O-{[L-1-(D-1-carbamoylmethyl-carbamoyl-3-carboxypropyl)-carbamoylethyl]-carbamoylmethyl}-2-deoxy-D-glucose, 2-benzamido-2-deoxy-3-O-{[L-1-(D-1-carbamoyl-3-carboxy-propyl)-carbamoyl-propyl]-carbamoylmethyl}-D-glucopyranose, 3-O-{[L-1-(D-1-carbamoyl-3-carboxypropyl)-carbamoylethyl]-carbamoylmethyl}-2-deoxy-2-propionamido-D-glucose, 2-acetamido-3-O-{[L-1-(D-1-carbamoyl-3-carboxy-propyl)-carbamoylpropyl]-carbamoylmethyl}-2-deoxy-D-glucose, 2-acetamino-3-O-{[L-1-(D-1-carbamoyl-3-carboxy-propyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{D-1-[L-1-carbamoyl-3-carboxy-propyl)-carbamoyl-2′-methyl-propyl]-carbamoylethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-acetamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{D-1-[L-1-(D-1-carbamoyl-3-(L-1-carboxy-ethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-(D-1-carbamoyl-3-carboxy-propyl)-carbamoyl-methyl]-N-methyl-carbamoylmethyl}-2-deoxy-D-glucose and 2-benzoylamino-3-O-{[L-1-(D-1-carbamoyl-3-carboxy-propyl)-carbamoyl-2′-methyl-propyl]-carbamoylmethyl}-2-deoxy-D-glucose.

EXAMPLE 8

Ovine erythrocyte membranes coupled to the compounds shown below are obtained analogously to Example 3: 2-acetamino-3-O-{D-1-[L-1-(D-1-carbamoyl-3-carboxypropyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-desoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{D-1-[L-1-(D-1-carbamoyl-3-(L-1-carboxy-ethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-1-(D-1-carbamoyl-3-carboxy-propyl)-carbamoyl-2′-methyl-propyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-desoxy-D-glucose, 2-acetamino-3-O-{[L-1-(D-1-carbamoyl-3-carboxy-propyl)-carbamoyl-ethyl]-N-methyl-carbamoylmethyl}-2-deoxy-D-glucose and 2-acetamino-3-O-{D-1-[L-1-carbamoyl-3-carboxy-propyl)-carbamoyl-2′-methyl-propyl]-carbamoylethyl}-2-deoxy-D-glucose.

EXAMPLE 9

Merozoites of the malaria pathogen Plasmodium knowlesi coupled to the compounds shown below are obtained analogously to Example 5: 2-acetamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2′-methylpropyl]-carbamoylmethyl}-2-deoxy-D-glucose, 2-acetamino-3-O-{D-1-[L-1-(D-1-carbamoyl-3-(L-1-carboxyethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-

1-(D-1-carbamoyl-3-carboxy-propyl)-carbamoyl-2'-methyl-propyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoylmethyl}-2-deoxy-D-glucose, 2-acetamino-3-O-{[L-1-(D-1-carbamoyl-3-carboxy-propyl)-carbamoyl-ethyl]-N-methylcarbamoyl-methyl}-2-deoxy-D-glucose and 2-acetamino-3-O-{D-1-[L-1-carbamoyl-3-carboxy-propyl)-carbamoyl-2'-methyl-propyl]-carbamoylethyl}-2-deoxy-D-glucose.

EXAMPLE 10

$10^8$ canine mammary carcinoma cells are suspended in a solution of 100 mg of 2-acetamino-3-O-{D-1-[L-1-(D-1-carbamoyl-3-succinimido-oxycarbonyl-propyl)-carbamoylethyl]-carbamoyl-ethyl}-2-deoxy-D-glucose in 10 ml of phosphate-buffered physiological sodium chloride solution of pH 7.2. [The tumour cells are obtained by the method of H. H. Sedlacek, H. Messmann and F. R. Seiler, Behring Inst. Mitt., No. 55, 349–355 (1974)]. The suspension is incubated for 90 minutes at room temperature. The tumour cell/muramyl-dipeptide conjugates are then sedimented by centrifuging and washed by resuspending in phosphate-buffered physiological sodium chloride solution and again centrifuging.

The quantitative determination of muramyl-dipeptide coupled to the tumour cells is carried out by means of the Morgan-Elson reaction (see Example 1) and indicates 60–80 μg of muramyl-dipeptide per $10^7$ mammary carcinoma cells.

EXAMPLE 11

Canine mammary carcinoma cells coupled to the compounds shown below are obtained analogously to Example 10: 2-acetamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{D-1-[L-1-(D-1-carbamoyl-3-carboxypropyl)-carbamoyl-ethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxy-propyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2'-methylpropyl]-carbamoylmethyl}-2-deoxy-D-glucose, 2-acetamino-3-O-{[D-1-[L-1-(D-1-carbamoyl-3-(L-1-carboxyethyl)-carbamoyl-propyl]-carbamoylethyl]-carbamoylethyl}-2-deoxy-D-glucose, 2-acetamino-3-O-{[L-1-(D-1,3-dicarboxy-propyl)-carbamoyl-2'-methyl-propyl]-carbamoylmethyl}-2-deoxy-D-glucose, 2-benzoylamino-3-O-{[L-1-(D-1-carbamoyl-3-carboxy-propyl)-carbamoyl-2'-methyl-propyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoylmethyl}-2-deoxy-D-glucose, 2-acetamino-3-O-{[L-1-(D-1-carbamoyl-3-carboxy-propyl)-carbamoyl-ethyl]-N-methylcarbamoyl-methyl}-2-deoxy-D-glucose and 2-acetamino-3-O-{D-1-[L-1-carbamoyl-3-carboxy-propyl)-carbamoyl-2'-methylpropyl]-carbamoylethyl}-2-deoxy-D-glucose.

EXAMPLE 12

100 mg of 2-acetamino-3-O-{[L-1-(D-1-carbamoyl-3-succinimido-oxycarbonyl-propyl)-carbamoyl-ethyl]-carbamoylmethyl}-2-deoxy-D-glucose are added to 10 ml of a suspension of foot and mouth disease culture vaccine (Beringwerke) in phosphate-buffered physiological sodium chloride solution. The suspension is shaken for 4 hours at 4° C. The virus/muramyl-dipeptide conjugate is then sterile-filtered, freed from low molecular weight reaction products by dialysis against water, and freeze-dried. The quantitative determination of muramyldipeptide coupled to viruses is carried out by means of the Morgan-Elson reaction (see Example 1).

EXAMPLE 13

Foot and mouth disease vaccine coupled to the compounds shown below is obtained analogously to Example 12: 2-acetamino-3-O-{D-1-[L-1-(D-1-carbamoyl-3-carboxypropyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2'-methylpropyl]-carbamoylmethyl}-2-deoxy-D-glucose, 2-acetamino-3-O-{D-1-[L-1-(D-1-carbamoyl-3-(L-1-carboxy-ethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2'-methyl-propyl]-carbamoyl-methyl}-2-deoxy-D-glucose, 2-benzoylamino-3-O-{[L-1-(D-1-carbamoyl-3-carboxy-propyl)-carbamoyl-2'-methylpropyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-

(D-1-carbamoyl-3-carboxypropyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2'-methyl-propyl]-carbamoylethyl}-2-deoxy-D-glucose.

EXAMPLE 14

T-lymphoblasts of CBA/J mice coupled to the compounds shown below are obtained analogously to Example 6: 2-acetamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{D-1-[L-1-(D-1-carbamoyl-3-carboxypropyl)-carbamoyl-ethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoylmethyl}-2-deoxy-D-glucose, 2-acetamino-3-O-{[L-1-(D-1-carbamoyl-3-carboxy-propyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoylethyl]-carbamoylmethyl}-2-deoxy-D-glucose, 2-acetamino-3-O-{[L-1-(D-1-carbamoyl-3-carboxy-propyl)-carbamoyl-2'-methyl-propyl]-carbamoylmethyl}-2-deoxy-D-glucose, 2-acetamino-3-O-{D-1-[L-1-(D-1-carbamoyl-3-(L-1-carboxyethyl)-carbamoyl-propyl)-carbamoylethyl]-carbamoylethyl}-2-deoxy-D-glucose, 2-acetamino-3-O-{[L-1-(D-1,3-dicarboxypropyl)-carbamoyl-2'-methyl-propyl]-carbamoylmethyl}-2-deoxy-D-glucose, 2-benzoylamino-3-O-{[L-1-(D-1-carbamoyl-3-carboxy-propyl)-carbamoyl-2'-methyl-propyl]-carbamoylmethyl}-2-deoxy-D-glucose, 2-acetamino-3-O-{[L-1-(D-1-carbamoyl-3-carboxy-propyl)-carbamoyl-N,N-tetramethylene]-carbamoylmethyl}-2-deoxy-D-glucose, 2-acetamino-3-O-{[L-1-(D-1-carbamoyl-3-carboxy-propyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2'-methyl-propyl]-carbamoylethyl}-2-deoxy-D-glucose.

EXAMPLE 15

1 mg of bovine serum albumin/2-acetamino-3-O-{[L-1-(D-1-carbamoyl-3-carboxy-propyl)-carbamoyl-ethyl]-carbamoyl-methyl}-2-deoxy-D-glucose conjugate is dissolved in 0.1 ml of phosphate-buffered physiological sodium chloride solution (PBS); 0.1 ml of a 5% suspension of carboxymethylcellulose in PBS is mixed with this solution. The mixture is administered intramuscularly, in two equal portions, to guinea pigs.

EXAMPLE 16

$10^8$ T-lymphoblasts/2-acetamino-3-O-{[L-1-(D-carbamoyl-3-carboxy-propyl)-carbamoyl-ethyl]-carbamoyl-methyl}-2-deoxy-D-glucose conjugates (see Example 6) are suspended in 0.5 ml of phosphate-buffered physiological sodium chloride solution (PBS); 0.5 ml of a 5% suspension of carboxymethylcellulose in PBS is admixed to the suspension. 0.1 ml of the mixture is administered subcutaneously to each mouse.

EXAMPLE 17

100 mg (0.17 mmol) of 2-acetamino-3-O-{[L-1-(D-1-carbamoyl-3-succinimido-oxycarbonyl-propyl)-carbamoylethyl]-carbamoyl-methyl}-2-deoxy-D-glucose are added to 10 ml of a suspension of rabies-HDC vaccine (Behringwerke) in phosphate-buffered physiological sodium chloride solution. The virus concentration is $2\times10^7$ $LD_{50}$/mouse per ml of suspension. The suspension is shaken for 4 hours at 4° C. The muramyl-dipeptide/rabies-HDC vaccine conjugate is then sterile-filtered, freed from low molecular weight reaction products by dialysis against water, and freeze-dried.

EXAMPLE 18

Rabies-HDC vaccine (Behringwerke) coupled to the compounds shown below is obtained analogously to Example 17: 2-acetamino-3-O-{D-1-[L-1-(D-1-carbamoyl-3-carboxypropyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxy-propyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2'-methyl-propyl]-carbamoylmethyl}-2-deoxy-D-glucose, 2-acetamino-3-O-{D-1-[L-1-(D-1-carbamoyl-3-(L-1-carboxyethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2'-methyl-propyl]-carbamoylmethyl}-2-deoxy-D-glucose, 2-benzoylamino-3-O-{[L-1-(D-1-carbamoyl-3-carboxy-propyl)-carbamoyl-2'-methyl-propyl]-carbamoyl-methyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-(D-1-carbamoyl-3-carboxypropyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2'-methyl-propyl]-carbamoylethyl}-2-deoxy-D-glucose.

EXAMPLE 19

100 mg (0.17 mmol) of 2-acetamino-3-O-{[L-1-(D-1-carbamoyl-3-succinimido-oxycarbonyl-propyl)-carbamoylethyl]-carbamoyl-methyl}-2-deoxy-D-glucose are added to 10 ml of a suspension of extracted influenza virus antigens of type A/Victoria/3/75 in phosphate-buffered physiological sodium chloride solution. (The virus antigens are obtained by the Tween/ether splitting process of Behringwerke, Marburg, Federal Republic of Germany, analogously to the preparation of ®Begrivac S; the concentration is 4,000 I.U. per ml of suspension). The suspension is shaken for 4 hours at 40° C. The virus antigen/muramyl-dipeptide conjugates are then freed from low molecular weight reaction products by dialysis against phosphate-buffered physiological sodium chloride solution; the dialysed suspension is frozen and stored at −20° C. until required for use.

EXAMPLE 20

Influenza virus antigen coupled to the compounds shown below is obtained analogously to Example 20: 2-acetamino-3-O-{D-1-[L-1-(D-1-carbamoyl-3-carboxy-propyl)-carbamoyl-ethyl]-carbamoyl-ethyl}-2-deoxy-D-glucose, 2-benzoylamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{L-1-(D-1-carbamoyl-3-carboxy-propyl)-carbamoylethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxypropyl)-carbamoylethyl]-carbamoylmethyl}-2-deoxy-D-glucose, 2-benzoylamino-3-O-{[L-1-(D-1-N-carbamoylmethylcarbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{D-1-[L1-(D-1-carbamoyl-3-(L-1-carboxyethyl)-carbamoylpropyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-(D-1-carbamoyl-3-carboxy-propyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2′-methyl-propyl]-carbamoylethyl}-2-deoxy-D-glucose.

EXAMPLE 21

10 mg of 2-acetamido-3-O-{[L-1-(D-1-carbamoyl-3-succinimido-oxycarbonyl-propyl)-carbamoyl-ethyl]-carbamoyl-methyl}-2-deoxy-D-glucose are added to 2 ml of a solution of tetanus toxoid in phosphate-buffered physiological sodium chloride solution. The toxoid concentration is 3 mg/ml. The solution is stirred for 4 hours at 4° C. The tetanus toxoid/muramyl-dipeptide conjugate is then freed from low molecular weight reaction products by ultrafiltration; the ultrafiltered solution is frozen and stored at −20° C. until required for use. Quantitative determination (Morgan-Elson reaction) indicates about 50 μg of muramyl-dipeptide per mg of tetanus toxoid/muramyl-dipeptide conjugate.

EXAMPLE 22

Tetanus toxoid coupled to the compounds shown below is obtained analogously to Example 21: 2-acetamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{[L-1-(D-1-carbamoyl-3-carboxy-propyl)-carbamoyl-ethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxypropyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carboamoylmethyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2′-methylpropyl]-carbamoylmethyl}-2-deoxy-D-glucose, 2-acetamino-3-O-{D-1-[L-1-(D-1-carbamoyl-3-(L-1-carboxyethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-(D-1-carbamoyl-3-carboxy-propyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2′-methyl-propyl]-carbamoylethyl}-2-deoxy-D-glucose.

EXAMPLE 23

50 mg of 2-acetamido-3-O-{[L-1-(D-1-carbamoyl-3-succinimido-oxycarbonyl-propyl)-carbamoyl-ethyl]-carbamoylmethyl}-2-deoxy-D-glucose are added to 10 ml of a solution of cholera toxoid from Vibrio cholerae in phosphate-buffered physiological sodium chloride solution. The protein concentration in the solution is 0.6 mg/ml. The solution is stirred for 4 hours at 4° C. The cholera toxoid/muramyl-dipeptide conjugate is then freed from low molecular weight reaction products by ultrafiltration; the ultrafiltered solution is frozen and stored at −20° C. until required for use. Quantitative determination (Morgan-Elson reaction) indicates 40-50 μg of muramyldipeptide per mg of cholera toxoid/-muramyl-dipeptide conjugate.

EXAMPLE 24

Tetanus toxoid coupled to the compounds shown below is obtained analogously to Example 23: 2-acetamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{D-1-[L-1-(D-1-carbamoyl-3-carboxy-propyl)-carbamoylethyl}-carbamoyl-ethyl}-2-deoxy-D-glucose, 2-benzoylamino-3-O-{[L-1-(D-1-carbamoyl-3-carboxy-propyl)-carbamoylethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoylpropyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxy-propyl)-carbamoylethyl]-carbamoylmethyl}-2-deoxy-D-glucose, 2-benzoylamino-3-O-{[L-1-(D-1-N-carbamoyl-methyl-carbamoyl-3-carboxy-propyl)-carbamoyl-ethyl]-carbamoylmethyl}-2-deoxy-D-glucose, 2-acetamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{D-1-[L-1-(D-1-carbamoyl-3-(L-1-carboxy-ethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-1-(D-1-carbamoyl-3-carboxy-propyl)-carbamoyl-2′-methyl-propyl]-carbamoyl-methyl}-2-deoxy-D-glucose, 2-acetamino-3-O-{[L-1-(D-1-carbamoyl-3-carboxypropyl)-carbamoyl-N,N-tetramethylene]-carbamoyl-methyl}-2-deoxy-D-glucose, 2-acetamino-3-O-{[L-1-(D-1-carbamoyl-3-carboxy-propyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2′-methyl-propyl]-carbamoylethyl}-2-deoxy-D-glucose.

EXAMPLE 25

20 mg of a synthetic eicosapeptide, which is identical with the C-terminal sequence of human choriongonadotropin (HCG) [literature: C. H. Schneider, K. Blaser, Ch. Pfeuti and E. Gruden, Febs Letters, 50, 272 (1975)] and 30 mg of 2-acetamido-3-O-{[L-1-(D-1-carbamoyl-3-succinimido-oxycarbonyl-propyl)-carbamoyl-ethyl]-carbamoyl-methyl}-2-deoxy-D-glucose are dissolved in 2 ml of sodium phosphate buffer solution of pH 7.2. The solution is stirred for 6 hours at room temperature. The eicosapeptide/muramyl-dipeptide conjugate is then isolated by chromatography on a Sephadex G-25 column (size 1.4×40 cm), with water as the eluent, and is freeze-dried. Quantitative aminoacid analysis shows that 1 muramyldipeptide molecule is bound to 1 eicosapeptide molecule.

EXAMPLE 26

The C-terminal eicosapeptide fragment of human choriongonadotropin coupled to the compounds shown below is obtained analogously to Example 25: 2-acetamino-3-O-{D-1-(D-1-carbamoyl-3-carboxy-propyl)-carbamoylethyl]-carbamoyl-ethyl}-2-deoxy-D-glucose, 2-benzoylamino-3-O-{D-1-[L-1-(D-1-carbamoyl-3-carboxy-propyl)-carbamoylethyl]-carbamoyl-ethyl}-2-deoxy-D-glucose, 2-benzoylamino-3-O-{[L-1-(D-1-carbamoyl-3-carboxy-propyl)-carbamoylethyl]-carbamoylmethyl}-2-deoxy-D-glucose, 2-benzoylamino-3-O-{[L-1-(D-1,3-dicarboxy-propyl)-carbamoylethyl]-carbamoylmethyl}-2-deoxy-D-glucose, 2-propionylamino-3-O-{[L-1-(D-1-carbamoyl-3-carboxy-propyl)-carbamoylethyl]-carbamoylmethyl}-2-deoxy-D-glucose, 2-acetamino-3-O-{[L-1-(D-1-N-carbamoylmethylcarbamoyl-3-carboxy-propyl)-carbamoylethyl]-carbamoylmethyl}-2-deoxy-D-glucose, 2-benzoylamino-3-O-{[L-1-(D-1-carbamoyl-3-carboxy-propyl)-carbamoyl-propyl]-carbamoylmethyl}-2-deoxy-D-glucose, 2-acetylamino-3-O-{[L-1-(D-1-carbamoyl-3-carboxy-propyl)-carbamoylpropyl]-carbamoyl-methyl}-2-deoxy-D-glucose, 2-acetamino-3-O-{[L-1-(D-1-carbamoyl-3-carboxypropyl)-carbamoyl-2-hydroxyethyl]-carbamoylmethyl}-2-deoxy-D-glucose, 2-propionylamino-3-O-{[L-1-(D-1,3-dicarboxypropyl)-carbamoylethyl]-carbamoylmethyl}-2-deoxy-D-glucose, 2-benzoylamino-3-O-{[L-1-(D-1-N-carbamoylmethylcarbamoyl-3-carboxy-propyl)-carbamoyl-ethyl}-carbamoylmethyl}-2-deoxy-D-glucose, 2-acetamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{D-1-[L-1-(D-1-carbamoyl-3-(L-1-carboxy-ethyl)-carbamoyl-propyl)-carbamoylethyl]-carbamoylethyl}-2-deoxy-D-glucose, 2-acetamino-3-O-{[L-1-(D-1,3-dicarboxy-propyl)-carbamoyl-2′-methyl-propyl]-carbamoyl-methyl}-2-deoxy-D-glucose, 2-benzoylamino-3-O-{[L-1-(D-1-carbamoyl-3-carboxy-propyl)-carbamoyl-2′-methyl-propyl]-carbamoylmethyl}-2-deoxy-D-glucose, 2-acetamino-3-O-{[L-1-(D-1-carbamoyl-3-carboxy-propyl)-carbamoyl-N,N-tetramethylene]-carbamoyl-methyl}-2-deoxy-D-glucose, 2-acetamino-3-O-{[L-1-(D-1-carbamoyl-3-carboxy-propyl)-carbamoyl-ethyl]-N-methyl-carbamoyl-methyl}-2-deoxy-D-glucose and 2-acetamino-3-O-{D-1-[L-1-carbamoyl-3-carboxy-propyl)-carbamoyl-2′-methyl-propyl]-carbamoylethyl}-2-deoxy-D-glucose.

EXAMPLE 27

Bovine serum albumin coupled to the compounds shown below is obtained analogously to Example 1: 2-acetamino-3-O-{[(D-1-carbamoyl-3-carboxy-propyl)-carbamoyl-methyl]-N-methyl-carbamoyl-methyl}-2-deoxy-D-glucose, 2-benzoylamino-3-O-{[D-1-carbamoyl-3-carboxypropyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoylmethyl}-2-deoxy-D- glucose, 2-acetamino-3-O-{[L-1-(D-1-carbamoyl-3-carboxy-propyl)-carbamoyl]-N-methylcarbamoyl-methyl}-2-deoxy-D-glucose, 2-acetamino-3-O-{[L-1-(D-1-carbamoyl-3-carboxy-propyl)-carbamoyl-propyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N ethyl-carbamoyl-methyl}-2-deoxy-D-glucose, 2-acetamino-3-O-{L-1-(D-1-carbamoyl-3-carboxy-propyl)-carbamoyl-ethyl]-N-propyl-carbamoylmethyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxypropyl)-carbamoyl-methyl]-N-methyl-carbamoyl-ethyl}-2-deoxy-D-glucose, 2-benzylamino-3-O-{D-1-[(D-1-carbamoyl-3-carboxy-propyl)-carbamoyl-methyl]-N-methyl-carbamoylethyl}-2-deoxy-D-glucose, 2-acetamino-3-O-{D-1-[L-1-(D-1-carbamoyl-3-carboxy-propyl)-carbamoyl-ethyl]-N-ethylcarbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoylethyl}-2-deoxy-D-glucose, 2-acetamino-3-O-{D-1-[L-1-(D-1-carbamoyl-3-carboxy-propyl)-carbamoyl-ethyl]-N-propylcarbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxy-methyl-phenyl]-carbamoylmethyl}-2-deoxy-D-glucose, 2-benzoylamino-3-O-{[L-1-(D-1-carbamoyl-3-carboxy-methyl-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-3-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxysuccinamido)-3-O-{[L-1-(D-1-carbamoyl-3-carboxy-propyl)-carbamoyl-ethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2'-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxypropyl)-carbamoyl-ethyl]-carbamoyl-methyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoylethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-dicarboxy-propyl)-N-methyl-carbamoyl-ethyl]-carbamoylmethyl}-2-deoxy-D-glucose.

EXAMPLE 28

Ovine erythrocyte membranes coupled to the compounds shown below are obtained analogously to Example 3: 2-acetamino-3-O-{[D-1-carbamoyl-3-carboxy-propyl)-carbamoyl-methyl]-N-methyl-carbamoyl-methyl}-2-deoxy-D-glucose, 2-benzoylamino-3-O-{[(D-1-carbamoyl-3-carboxypropyl)-carbamoyl-methyl]-N-methyl-carbamoyl-methyl}-2-deoxy-D-glucose, 2-acetamino-3O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoylmethyl}-2-deoxy-D-glucose, 2-acetamino-3-O-{[L-1-(D-1-carbamoyl-3-carboxy-propyl)-carbamoyl-propyl]-N-ethylcarbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoylethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoylmethyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamloyl-ethyl}-2-deoxy-D-glucose, 2-benzoylamino-3-O-[D-1-[(D-1-carbamoyl-3-carboxy-propyl)-carbamoyl-methyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoylethyl}-2-deoxy-D-glucose, 2-acetamino-3-O-{D-1-[L-1-(D-1-carbamoyl-3-carboxy-propyl)-carbamoyl-propyl]-N-ethyl-carbamoylmethyl}-2-deoxy-D-glucose, 2-benzamido-3-O-{D-1-[L-1-(D-1-carbamoyl-3-carboxy-propyl)-carbamoylpropyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoylethyl}-2-deoxy-D-glucose, 2-acetamino-3-O-{D-1-[L-1-(D-1-carbamoyl-3-carboxy-propyl)-carbamoyl-N,N-pentamethylene]-carbamoylethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxymethyl-phenyl]-carbamoyl-methyl}-2-deoxy-D-glucose, 2-benzoylamino-3-O-{[L-1-(D-1-carbamoyl-3-carboxy-methylphenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxysuccinamido)-3-O-{D-1-[L-1-(D-1-carbamoyl-3-carboxypropyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxypropyl)-carbamoyl-2′-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2′-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-}D-1-[L-1-(D-1-carbamoyl-3-carboxypropyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoylmethyl}-2-deoxy-D-glucose, 2-(N-methyl-acetamino)-3-O-{D-1-[L-1-(D-1-carbamoyl-3-carboxy-propyl)-carbamoylethyl]-carbamoyl-ethyl}-2-deoxy-D-glucose, 2-acetamino-3-O-{D-1-[L-1-(D-1-carbamoyl-3-carboxy-propyl)-carbamoyl-2′-phenylethyl]-carbamoyl-ethyl}-2-deoxy-D-glucose, 2-acetamino-3-O-{[L-1-(D-1-carbamoyl-3-carboxy-propyl)-carbamoyl-2′-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoylethyl]-carbamoylmethyl}-2-deoxy-D-glucose and 2-acetamino-3-O-{[L-1-(D-1,3-di-carboxy-propyl)-N-methylcarbamoyl-ethyl]-carbamoylmethyl}-2-deoxy-D-glucose.

EXAMPLE 29

Group C-polysaccharide of Neisseria meningitidis coupled to the compounds shown below is obtained analogously to Example 4: 2-acetamino-3-O-{[(D-1-carbamoyl-3-carboxy-propyl)-carbamoyl-methyl]-N-methyl-carbamoylmethyl}-2-deoxy-D-glucose, 2-benzoylamino-3-O{[(D-1-carbamoyl-3-carboxy-propyl)-carbamoyl-methyl]-N-methylcarbamoyl-methyl}-2-deoxy-D-glucose, 2-acetamino-3-O-{[L-1-(D-1-carbamoyl-3-carboxy-propyl)-carbamoyl-ethyl)-N-ethyl-carbamoyl-methyl}-2-deoxy-D-glucose, 2-acetamino-3-O-{[L-1-(D-1-carbamoyl-3-carboxy-propyl)-carbamoylpropyl]-N-methyl-carbamoyl-methyl}-2-deoxy-D-glucose, 2-acetamino-3-O-{[L-1-(D-1-carbamoyl-3-carboxy-propyl)-carbamoyl-propyl]-N-ethyl-carbamoylmethyl}-2-deoxy-D-glucose, 2-benzamido-3-O-{[L-1-(D-1-carbamoyl-3-carboxypropyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoyl-ethyl]-N-propyl-carbamoylmethyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoylmethyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoylethyl}-2-deoxy-D-glucose, 2-benzoylamino-3-O-{D-1-[(D-1-carbamoyl-3-carboxy-propyl)-carbamoylmethyl]-N-methyl-carbamoylethyl}-2-deoxy-D-glucose, 2-acetamino-3-O-{D-1-[L-1-(D-1-carbamoyl-3-carboxy-propyl)-carbamoyl-ethyl]-N-ethylcarbamoylethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoylpropyl]-N-ethyl-carbamoylmethyl}-2-deoxy-D-glucose, 2-benzamido-3-O-{D-1-[L-1-(D-1-carbamoyl-3-carboxy-propyl)-carbamoylpropyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoylethyl}-2-deoxy-D-glucose, 2-acetamino-3-O-{D-1-[L-1-(D-1-carbamoyl-3-carboxy-propyl)-carbamoyl-N,N-pentamethylene]-carbamoylethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxymethyl-phenyl]-carbamoyl-methyl}-2-deoxy-D-glucose, 2-benzoylamino-3-O-{[L-1-(D-1-carbamoyl-3-carboxy-methylphenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoylethyl}-2-deoxy-D-glucose, 2-(β-carbomethoxysuccinamido)-3-O-{[L-1-(D-1-carbamoyl-3-carboxy-propyl)-carbamoylethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoyl-methyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxypropyl]-carbamoyl-ethyl}-2-deoxy-D-glucose, 2-acetamino-3-O-{D-1-[L-1-(D-1-carbamoyl-3-carboxy-propyl)-carbamoyl-2'-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoylethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxypropyl)-carbamoyl-2'-(p-hyroxyphenyl)-ethyl]-carbamoylmethyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methylcarbamoyl-ethyl]-carbamoylmethyl}-2-deoxy-D-glucose.

EXAMPLE 30

Merozoites of the malaria pathogen Plasmodium knowlesi coupled to the compounds shown below are obtained analogously to Example 5: 2-acetamino-3-O-{[(D-1-carbamoyl-3-carboxy-propyl)-carbamoyl-methyl]-N-methyl-carbamoyl-methyl}-2-deoxy-D-glucose, 2-benzoylamino-3-O-{[(D-1-carbamoyl-3-carboxy-propyl)-carbamoyl-methyl]-N-methylcarbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoyl-methyl}-2-deoxy-D-glucose, 2-acetamino-3-O-{[L-1-(D-1-carbamoyl-3-carboxy-propyl)-carbamoylpropyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxypropyl)-carbamoyl-ethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoylethyl]-carbamoyl-methyl}-2-deoxy-D-glucose, 2-acetamino-3-O-{D-1-[(D-1-carbamoyl-3-carboxy-propyl)-carbamoylmethyl]-N-methyl-carbamoyl-ethyl}-2-deoxy-D-glucose, 2-benzoylamino-3-O-{D-1-[(D-1-carbamoyl-3-carboxy-propyl)-carbamoyl-methyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-propyl]-N-methylcarbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxymethyl-phenyl]-carbamoyl-methyl}-2-deoxy-D-glucose, 2-benzoylamino-3-O-{[L-1-(D-1-carbamoyl-3-carboxy-methylphenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxypropyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxysuccinamido)-3-O-{D-1-[L-1-(D-1-carbamoyl-3-carboxypropyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2'-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxypropyl)-carbamoyl-ethyl]-carbamoyl-ethyl}-2-deoxy-D-glucose, 2-glycolylamino-3-O-{[L-1-(D-1-carbamoyl-3-carboxypropyl)-carbamoyl-ethyl]-carbamoyl-methyl}-2-deoxy-D-glucose, 2-(N-methyl-acetamino)-3-O-{[L-1-(D-1-carbamoyl-3-carboxypropyl)-carbamoyl-ethyl]-carbamoylmethyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methyl-carbamoyl-ethyl]-carbamoylmethyl}-2-deoxy-D-glucose.

EXAMPLE 31

T-Lymphoblasts of CBA/J mice coupled to the compounds shown below are obtained analogously to Example 6: 2-acetamino-3-O-{[(D-1-carbamoyl-3-carboxy-propyl)-carbamoyl-methyl]-N-methyl-carbamoyl-methyl}-2-deoxy-D-glucose, 2-benzoylamino-3-O-{[(D-1-carbamoyl-3-carboxypropyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl}-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoylmethyl}-2-deoxy-D-glucose, 2-acetamino-3-O-{[L-1-(D-1-carbamoyl-3-carboxy-propyl)-carbamoyl-propyl]-N-ethylcarbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoylethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzylamino-3-O-{[L-1-(D-1-carbamoyl-3-carboxy-propyl)-carbamoyl-N,N-pentamethylene]-carbamoylmethyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoylmethyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxypropyl)-carbamyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethylcarbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxypropyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoylethyl}-2-deoxy-D-glucose, 2-acetamino-3-O-{[L-1-(D-1-carbamoyl-3-carboxy-methyl)-phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxypropyl)-carbamoyl-2-methyl-mercapto-ethyl]-carbamoylmethyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxypropyl)-carbamoylethyl]-carbamoyl-ethyl}-2-deoxy-D-glucose, 2-(β-carbomethoxysuccinamido)-3-O-{[L-1-(D-1-carbamoyl-3-carboxy-propyl)-carbamoyl-ethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-carbamoyl-3-trimethylsilyl-carboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoylethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxy-propyl]-carbamoylethyl}-2-deoxy-D-glucose, 2-acetamino-3-O-{D-1-[L-1-(D-1-carbamoyl-3-carboxy-propyl)-carbamoyl-2'-(p-hydroxyphenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoylmethyl}-2-deoxy-D-glucose, 2-(N-methyl-acetamino)-3-O-{D-1-[L-1-(D-1-carbamoyl-3-carboxy-propyl)-carbamoylethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoylethyl]-carbamoylmethyl}-2-deoxy-D-glucose and 2-acetamino-3-O-{[L-1-(D-1,3-di-carboxy-propyl)-N-methylcarbamoyl-ethyl]-carbamoylmethyl}-2-deoxy-D-glucose.

EXAMPLE 32

Foot and mouth disease culture vaccine (Beringwerke) coupled to the compounds shown below is obtained analogously to Example 12: 2-acetamino-3-O-{[(D-1-carbamoyl-3-carboxy-propyl)-carbamoyl-methyl]-N-methylcarbamoyl-methyl}-2-deoxy-D-glucose, 2-benzoylamino-3-O-{[(D-1-carbamoyl-3-carboxy-propyl)-carbamoyl-methyl]-N-methyl-carbamoyl-methyl}-2-deoxy-D-glucose, 2-acetamino-3-O-{[L-1-

(D-1-carbamoyl-3-carboxy-propyl)-carbamoylethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoyl-methyl}-2-deoxy-D-glucose, 2-acetamino-3-O-{[L-1-(D-1-carbamoyl-3-carboxypropyl)-carbamoyl-propyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N-ethyl-carbamoylmethyl}-2-deoxy-D-glucose, 2-acetamino-3-O-{[L-1-(D-1-carbamoyl-3-carboxy-propyl)-carbamoyl-ethyl]-N-propylcarbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxypropyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoylethyl}-2-deoxy-D-glucose, 2-benzoylamino-3-O-{D-1-[(D-1-carbamoyl-3-carboxy-propyl)-carbamoyl-methyl]-N-methylcarbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoylpropyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-(D-1-carbamoyl-3-carboxy-propyl)-carbamoyl-ethyl]-N-propylcarbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxy-methyl)-phenyl]-carbamoyl-methyl}-2-deoxy-D-glucose, 2-benzoylamino-3-O-{[L-1-(D-1-carbamoyl-3-carboxymethyl)-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoylethyl}-2-deoxy-D-glucose, 2-(β-carbomethoxy-succinamido)-3-O-{[L-1-(D-1-carbamoyl-3-carboxy-propyl)-carbamoylethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoylethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2′-hydroxy-propyl]-carbamoylethyl}-2-deoxy-D-glucose, 2-acetamino-3-O-{D-1-[L-1-(D-1-carbamoyl-3-carboxy-propyl)-carbamoyl-2′-(p-hydroxyphenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoylmethyl}-2-deoxy-D-glucose, 2-(N-methyl-acetamino)-3-O-{D-1-[L-1-(D-1-carbamoyl-3-carboxy-propyl)-carbamoylethyl]-carbamoyl-ethyl}-2-deoxy-D-glucose, 2-acetamino-3-O-{D-1-[L-1-(D-1-carbamoyl-3-carboxy-propyl)-carbamoyl-2′-phenylethyl]-carbamoyl-ethyl}-2-deoxy-D-glucose, 2-acetamino-3-O-{[L-1-(D-1-carbamoyl-3-carboxy-propyl)-carbamoyl-2′-(p-hydroxyphenyl)-ethyl]-carbamoyl-methyl}-2-deoxy-D-glucose, 2-acetamino-3-O-{[L-1-(D-1-[L-1-carboxyethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methyl-carbamoyl-ethyl]-carbamoylmethyl}-2-deoxy-D-glucose.

EXAMPLE 33

Rabies-HDC vaccine (Beringwerke) coupled to the compounds shown below is obtained analogously to Example 17: 2-acetamino-3-O-{[(D-1-carbamoyl-3-carboxy-propyl)-carbamoyl-methyl]-N-methyl-carbamoyl-methyl}-2-deoxy-D-glucose, 2-benzoylamino-3-O-{[(D-1-carbamoyl-3-carboxypropyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoylmethyl}-2-deoxy-D-glucose, 2-acetamino-3-O-{[L-1-(D-1-carbamoyl-3-carboxy-propyl)-carbamoyl-propyl]-N-ethylcarbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoylethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoylmethyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoylmethyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoylethyl}-2-deoxy-D-glucose, 2-acetamino-3-O-{D-1-[L-1-(D-1-carbamoyl-3-carboxypropyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethylcarbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxypropyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoylethyl}-2-deoxy-D-glucose, 2-acetamino-3-O-{]L-1-(D-1-carbamoyl-3-carboxy-methyl)-phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxypropyl)-carbamoyl-2-methyl-mercapto-ethyl]-carbamoylmethyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxypropyl)-carbamoylethyl]-carbamoyl-ethyl}-2-deoxy-D-glucose, 2-(β-carbomethoxysuccinamido)-3-O-{[L-1-(D-1-carbamoyl-3-carboxy-propyl)-carbamoyl-ethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O{[L-1-(D-1-carbamoyl-3-trimethylsilylcarboxy-propyl)-carbamoyl-ethyl]-carbamoylmethyl}-2-deoxy-1,4,6-tris-trimethylsilyl-D-glucose (on contact with water the trimethylsilyl ester group is rapidly hydrolysed), 2-acetamino-2-desoxy-3-O-{[L-1-(D-1-carbamoyl-3-trimethylsilylcarboxy-propyl)-carbamoylethyl]-carbamoylmethyl}-1,4,6-tris-trimethylsilyl-D-glucose, 2-acetamino-3-O-{D-1-[L-1-(D-1-carbamoyl-3-carboxypropyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2′-hydroxy-propyl]-carbamoylethyl}-2-deoxy-D-glucose, 2-acetamino-3-O-{D-1-[L-1-(D-1-carbamoyl-3-carboxy-propyl)-carbamoyl-2′-(p-hydroxyphenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-cabamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxypropyl)-carbamoyl-ethyl]-carbamoylmethyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2′-phenylethyl]-carbamoyl-ethyl}-2-deoxy-D-glucose, 2-acetamino-3-O-{[L-1-(D-1-carbamoyl-3-carboxy-propyl)-carbamoyl-2′-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methyl-carbamoyl-ethyl]-carbamoylmethyl}-2-deoxy-D-glucose.

EXAMPLE 34

Influenza virus antigens of type A/Victoria/3/75 coupled to the compounds shown below are obtained analogously to Example 19: 2-acetamino-3-O-{[D-1-carbamoyl-3-carboxy-propyl)-carbamoyl-methyl]-N-methyl-carbamoylmethyl}-2-deoxy-D-glucose, 2-benzoylamino-3-O-{[D-1-carbamoyl-3-carboxy-propyl)-carbamoyl-methyl]-N-methylcarbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoyl-methyl}-2-deoxy-D-glucose, 2-acetamino-3-O-{[L-1-(D-1-carbamoyl-3-carboxy-propyl)-carbamoyl-propyl]-N-ethyl-carbamoyl-methyl}-2-deoxy-D-glucose, 2-benzamido-3-O-{[L-1-(D-1-carbamoyl-3-carboxypropyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoyl-ethyl]-N-propyl-carbamoylmethyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoyl-methyl]-N-methyl-carbamoylethyl}-2-deoxy-D-glucose, 2-acetamino-3-O-{D-1-[L-1-(D-1-carbamoyl-3-carboxy-propyl)-carbamoyl-ethyl]-N-ethylcarbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoylpropyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoylethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxymethyl)-phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-

2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxysuccinamido)-3-O-{D-1-[L-1-(D-1-carbamoyl-3-carboxypropyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoyl-methyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilyl-carboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl}-carbamoyl-ethyl}-2-deoxy-D-glucose, 2-acetamino-3-O-{D-1-[L-1-(D-1-carbamoyl-3-carboxy-propyl)-carbamoyl-2′-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2′-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxypropyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{D-1-[L-1-(D-1carbamoyl-3-carboxy-propyl)-carbamoyl-ethyl]-carbamoylethyl}-2-deoxy-D-glucose, 2-acetamino-3-O-{D-1-[L-1-(D-1-carbamoyl-3-carboxy-propyl)-carbamoyl-2′-phenylethyl]-carbamoyl-ethyl}-2-deoxy-D-glucose, 2-acetamino-3-O-{[L-1-(D-1-carbamoyl-3-carboxy-propyl)-carbamoyl-2′-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-dicarboxy-propyl)-N-methyl-carbamoyl-ethyl]-carbamoylmethyl}-2-deoxy-D-glucose.

EXAMPLE 35

Tetanus toxoid coupled to the compounds shown below is obtained analogously to Example 21: 2-acetamino-3-O-{[(D-1-carbamoyl-3-carboxy-propyl)-carbamoyl-methyl]-N-methyl-carbamoyl-methyl}-2-deoxy-D-glucose, 2-benzoyl-amino-3-O-{[(D-1-carbamoyl-3-carboxy-propyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoyl-methyl}-2-deoxy-D-glucose, 2-acetamino-3-O{[L-1-(D-1-carbamoyl-3-carboxy-propyl)-carbamoyl-propyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O -{[L-1-(D-1-carbamoyl-3-carboxy-propyl)-carbamoyl-ethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoyl-methyl]-N-methyl-carbamoyl-ethyl}-2-deoxy-D-glucose, 2-acetamino-3-O -{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{L-1-(D-1-carbamoyl-3-carboxy-methyl)-phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxysuccinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoyl-methyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2′-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2′-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methyl-carbamoyl-ethyl]-carbamoylmethyl}-2-deoxy-D-glucose.

EXAMPLE 36

Cholera toxoid from Vibrio cholerae coupled to the compounds shown below is obtained analogously to Example 23: 2-acetamino-3-O-{[(D-1-carbamoyl-3-carboxy-propyl)-carbamoyl-methyl]-N-methyl-carbamoyl-methyl}-2-deoxy-D-glucose, 2-benzoylamino-3-O-{[(D-1-carbamoyl-3-carboxy-propyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-}[L-1-(D-1-carbamoyl-3-carboxy-propyl)-carbamoyl-propyl]-N-methyl-carbamoyl-methyl}-2-deoxy-D-glucose, 2-acetamino-3-O-{[L-1-(D-1-carbamoyl-3-carboxy-propyl)-carbamoyl-propyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoyl-ethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoyl-methyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-[L-1-(D-1--carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxy-methyl)-phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilyl-carboxy-propyl)-carbamoyl-ethyl]-carbamoyl-methyl}-2-deoxy-1,4,6-tris-trimethylsilyl-D-glucose (on contact with water the trimethylsilyl ester group is repidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2'-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-di-carboxy-propyl)-N-methyl-carbamoyl-ethyl]-carbamoylmethyl}-2-deoxy-D-glucose.

EXAMPLE 37

A synthetic eicosapeptide, which is identical to the C-terminal sequence of human choriongonadotropin, coupled to the compounds shown below, is obtained analogously to Example 25: 2-acetamino-3-O-{[(D-1-carbamoyl-3-carboxy-propyl)-carbamoyl-methyl]-N- methyl-carbamoyl-methyl}-2-deoxy-D-glucose, 2-benzoylamino-3-O-{[(D-1-carbamoyl-3-carboxy-propyl)-carbamoyl-methyl]-N-methyl-carbamoyl-methyl}-2-deoxy-D-glucose, 2-acetamino-3-O-{[L-1-(D-1-carbamoyl-3-carboxy-propyl)-carbamoyl-ethyl]-N-ethyl-carbamoyl-methyl}-2-deoxy-D-glucose, 2-acetamino-3-O-{[L-1-(D-1-carbamoyl-3-carboxy-propyl)-carbamoyl-propyl]-N-methyl-carbamoyl-methyl}-2-deoxy-D-glucose, 2-acetamino-3-O-{[L-1-(D-1-carbamoyl-3-carboxy-propyl)-carbamoyl-propyl]-N-ethyl-carbamoyl-methyl}-2-deoxy-D-glucose, 2-benzamido-3-O-{[L-1-(D-1-carbamoyl-3-carboxy-propyl)-carbamoyl-propyl]-N-ethyl-carbamoyl-methyl}-2-deoxy-D-glucose, 2-acetamino-3-O-{[L-1-(D-1-carbamoyl-3-carboxy-propyl)-carbamoyl-ethyl]-N-propyl-carbamoyl-methyl}-2-deoxy-D-glucose, 2-acetamino-3-O-{[L-1-(D-1-carbamoyl-3-carboxy-propyl)-carbamoyl-N,N-pentamethylene]-carbamoyl-methyl}-2-deoxy-D-glucose, 2-benzoylamino-3-O-{[L-1-(D-1-carbamoyl-3-carboxy-propyl)-carbamoyl-N,N-pentamethylene]-carbamoyl-methyl}-2-deoxy-D-glucose, 2-acetamino-3-O-{[L-1-(D-1-carbamoyl-3-carboxy-propyl)-N-methyl-carbamoyl-ethyl]-carbamoyl-methyl}-2-deoxy-D-glucose, 2-acetamino-3-O-{D-1-[(D-1-carbamoyl-3-carboxy-propyl)-carbamoyl-methyl]-N-methyl-carbamoyl-ethyl}-2-deoxy-D-glucose, 2-benzoylamino-3-O-{D-1-[(D-1-carbamoyl-3-carboxy-propyl)-carbamoyl-methyl]-N-methyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-propyl]-N-methyl-carbamoyl-ethyl}-2-deoxy-D-glucose, 2-acetamino-3-O-{D-1-[L-1-(D-1-carbamoyl-3-carboxy-propyl)-carbamoyl-propyl]-N-ethyl-carbamoyl-methyl}-2-deoxy-D-glucose, 2-benzamido-3-O-{D-1-[L-1-(D-1-carbamoyl-3-carboxy-propyl)-carbamoyl-propyl]-N-ethyl-carbamoyl-ethyl}-2-deoxy-D-glucose, 2-acetamino-3-O-{D-1-[L-1-(D-1-carbamoyl-3-carboxy-propyl)-carbamoyl-ethyl]-N-propyl-carbamoyl-ethyl}-2-deoxy-D-glucose, 2-acetamino-3-O-{D-1-[L-1-(D-1-carbamoyl-3-carboxy-propyl)-carbamoyl-N,N-pentamethylene]-carbamoyl-ethyl}-2-deoxy-D-glucose, 2-benzoylamino-3-O-{D-1-[L-1-(D-1-carbamoyl-3-carboxy-propyl)-carbamoyl-N,N-pentamethylene]-carbamoyl-ethyl}-2-deoxy-D-glucose, 2-acetamino-3-O-{D-1-[L-1-(D-1-carbamoyl-3-carboxy-propyl)-N-methyl-carbamoyl-ethyl]-carbamoyl-ethyl}-2-deoxy-D-glucose, 2-acetamino-3-O-{[L-1-(D-1-carbamoyl-3-carboxy-methyl)phenyl]-carbamoyl-methyl}-2-deoxy-D-glucose, 2-benzoylamino-3-O-{[L-1-(D-1-carbamoyl-3-carboxy-methyl)-phenyl]-carbamoyl-methyl}-2-deoxy-D-glucose, 2-benzamino-3-O-{[L-1-(D-1-carbamoyl-3-carboxy-propyl)-carbamoyl-2-methyl-mercapto-ethyl]-carbamoyl-methyl}-2-deoxy-D-glucose, 2-benzamino-3-O-{[L-1-(D-1-carbamoyl-3-carboxy-propyl)-carbamoyl-2-chloroethyl]-carbamoyl-methyl}-2-deoxy-D-glucose, 2-acetamino-3-O-{D-1-[L-1-(D-1-carbamoyl-3,3-dicarboxy-propyl)-carbamoylethyl]-carbamoyl-ethyl}-2-deoxy-D-glucose, 2-(β-carbomethoxy-succinamido)-3-O-{[L-1-(D-1-carbamoyl-3-carboxy-propyl)-carbamoyl-ethyl]-carbamoyl-methyl}-2-deoxy-D-glucose, 2-(β-carbomethoxy-succinamido)-3-O-{D-1-[L-1-(D-1-carbamoyl-3-carboxy-propyl)-carbamoyl-ethyl]-carbamoyl-ethyl}-2-deoxy-D-glucose, 2-benzamino-3-O-{[L-1-(D-1-carbamoyl-3-trimethylsilylcarboxy-propyl)-carbamoyl-ethyl]-carbamoyl-methyl}-2-deoxy-1,4,6-tris-trimethylsilyl-D-glucose (on contact with water the trimethylsilyl ester group is rapidly hydrolysed), 2-acetamino-2-deoxy-3-O-{[L-1-(D-1-carbamoyl-3-trimethylsilylcarboxy-propyl)-carbamoyl-ethyl]-carbamoylmethyl}-1,4,6-tris-trimethylsilyl-D-glucose, 2-acetamino-3-O-{D-1-[L-1-(D-1-carbamoyl-3-carboxy-propyl)-carbamoyl-propyl]-carbamoyl-ethyl}-2-deoxy-D-glucose, 2-acetamino-3-O-{D-1-[L-1-(D-1-carbamoyl-3-carboxy-propyl)-carbamoyl-2'-hydroxy-propyl]-carbamoyl-ethyl}-2-deoxy-D-glucose, 2-acetamino-3-O-{D-1-[L-1-(D-1-carbamoyl-3-carboxy-propyl)-carbamoyl-2'-(p-hydroxy-phenyl)-ethyl]-carbamoyl-ethyl}-2-deoxy-D-glucose, 2-acetamino-3-O-{D-1-[L-1-(D-1-carbamoyl-3-carboxy-propyl)-carbamoyl-N,N-tetramethylene]-carbamoyl-ethyl}-2-deoxy-D-glucose, 2-glycolylamino-3-O-{D-1-[L-1-(D-1-carbamoyl-3-carboxy-propyl)-carbamoyl-ethyl]-carbamoyl-ethyl}-2-deoxy-D-glucose, 2-glycolylamino-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{[L-1-(D-1-carbamoyl-3-carboxy-propyl)-carbamoyl-ethyl]-carbamoyl-methyl}-2-deoxy-D-glucose, 2-(N-methyl-acetamino)-3-O-{D-1-[L-1-(D-1-carbamoyl-3-carboxy-propyl)-carbamoyl-ethyl]-carbamoyl-ethyl}-2-deoxy-D-glucose, 2-acetamino-3-O-{D-1-[L-1-(D-1-carbamoyl-3-carboxy-propyl)-carbamoyl-2'-phenylethyl]-carbamoyl-ethyl}-2-deoxy-D-glucose, 2-acetamino-3-O-{[L-1-(D-1-carbamoyl-3-carboxy-propyl)-carbamoyl-2'-(p-hydroxyphenyl)-ethyl]-carbamoyl-methyl}-2-deoxy-D-glucose, 2-acetamino-3-O-{[L-1-(D-1-[L-1-carboxy-ethyl]-carbamoyl-3-benzylcarboxy-propyl)-carbamoyl-ethyl]-carbamoylmethyl}-2-deoxy-D-glucose and 2-acetamino-3-O-{[L-1-(D-1,3-dicarboxy-propyl)-N-methyl-carbamoyl-ethyl]-carbamoyl-methyl}-2-deoxy-D-glucose.

Several of the muramyl-peptides mentioned above, and of their forms coupled with spacers, are novel. They can be obtained, for example, as described in the examples which follow:

EXAMPLE 38

A solution of 3.4 g of benzyl-2-acetamino-3-O-(D-1-{L-1-[D-1-carbamoyl-3-(L-1-carboxy-ethyl-carbamoyl)-propyl]-carbamoyl-ethyl}-carbamoyl-ethyl)-2-deoxy-α-D-glucopyranoside benzyl ester in 100 ml of a 2:1 mixture of methanol and distilled water is hydrogenated for 24 hours in the presence of 0.3 g of 10% palladium on charcoal under normal pressure, at 45° C. The catalyst is filtered off and the filtrate is evaporated. The residue is dissolved in 40 ml of water and this solution is extracted 3 times with, in each case, 40 ml of sec.-butanol saturated with water. The organic phases are then washed 3 times with 40 ml, each time, of water saturated with sec.-butanol. The aqueous solutions are combined and evaporated and the residue is dissolved in a small amount of distilled water and freeze-dried. This gives 2-acetamino-3-O-(D-1-{L-1-[D-1-carbamoyl-3-(L-1-carboxy-ethyl-carbamoyl)-propyl]-carbamoyl-ethyl}-carbamoyl-ethyl)-2-deoxy-D-glucose as a white powder of $[\alpha]_D^{20} = +9° \pm 1°$ (distilled water, c=1.090).

The starting material used is prepared as follows:

A solution of 6.1 g of benzyl-2-acetamino-3-O-{D-1-[L-1-(D-1-carbamoyl-3-carboxypropyl)-carbamoyl-ethyl]-carbamoyl-ethyl}-2-deoxy-α-D-glucopyranoside monohydrate and 3.5 g of L-alanine benzyl ester p-toluenesulfonate in 30 ml of N,N-dimethylformamide is treated with 1.4 ml of triethylamine, 1.1 g of N-hydroxy-succinimide and 2.3 g of dicyclohexylcarbodiimide and the mixture is stirred for 48 hours at room temperature. The dicyclohexylurea which has crystallised out is filtered off with suction and washed with 10 ml of N,N-dimethylformamide, and the filtrate is evaporated to dryness. The residue is suspended in 100 ml of water, the suspension is stirred for 1 hour at 0° C. and the insoluble material is filtered off with suction, washed with a small amount of ice water and dried. The product is then dissolved in methanol, precipitated with a two-fold amount of ethyl acetate, filtered off with suction, washed with a small amount of ethyl acetate and dried: $[\alpha]_D^{20}=+72°\pm1°$ (methanol, c=0.998).

Analogously, starting from benzyl-2-acetamino-3-O-{[L-1-(D-1-carbamoyl-3-carboxypropyl)-carbamoyl-ethyl]-carbamoyl-methyl}-2-deoxy-α-D-glucopyranoside, 2-acetamino-3-O-({L-1-[D-1-carbamoyl-3-(L-1-carboxy-ethyl-carbamoyl)-propyl]-carbamoyl-ethyl}-carbamoyl-methyl)-2-deoxy-D-glucose is obtained.

Starting from benzyl-3-O-{D-1-[L-1-(D-1-carbamoyl-3-carboxy-propyl)-carbamoyl-ethyl]-carbamoyl-ethyl}-2-deoxy-2-propionamino-α-D-glucopyranoside and glycine benzyl ester p-toluenesulfonate, 3-O-(D-1-{L-1-[D-1-carbamoyl-3-(carboxy-methyl-carbamoyl)-propyl]-carbamoyl-ethyl}-carbamoyl-ethyl)-2-deoxy-2-propionamino-D-glucose is prepared.

The following are prepared analogously: 2-acetamino-3-O-({L-1-[D-1-carbamoyl-3-(carboxyl-methyl-carbamoyl)-propyl]-carbamoyl-ethyl}-carbamoyl-methyl)-2-deoxy-D-glucose, 2-butyroylamino-3-O-(D-1-{L-1-[D-1-carbamoyl-3-(L-1-carboxy-ethyl-carbamoyl)-propyl]-carbamoyl-ethyl}-carbamoyl-ethyl -2-deoxy-D-glucose, ) 2-butyroylamino-3-O- {L-1-[D-1-carbomoyl-3-(L-1-carboxy-ethyl-carbamoyl)-propyl]-carbamoyl-ethyl}-carbamoyl-methyl -2-deoxy-D-glucose, 3-O-({L-1-[D-1-carbamoyl-3-(carboxy-methyl-carbamoyl)-propyl]-carbamoyl-ethyl}-carbamoyl-methyl)-2-deoxy-2-propionamino-D-glucose, 2-iso-butyroylamino-3-O- {L-1-[D-1-carbamoyl-3-(L-1-carboxy-ethyl-carbamoyl)-propyl]-carbamoyl-propyl}-carbamoyl-methyl)-2-deoxy-D-glucose, 2-iso-butyroylamino-3-O- D-1-{L-1-[D-1-carbamoyl-3-(L-1-carboxy-ethylcarbamoyl)-propyl]-carbamoyl-propyl}-carbamoyl-ethyl -2-deoxy-D-glucose, 2-iso-butyroylamino-3-O-({L-1-[D-1-carbamoyl-3-(L-1-carboxy-ethyl-carbamoyl)-propyl]-carbamoyl-2-methyl-propyl}-carbamoyl-methyl)-2-deoxy-D-glucose, 2-iso-butyroylamino-3-O-(D-1-{L-1-[D-1-carbamoyl-3-(L-1-carboxy-ethyl-carbamoyl)-propyl]-carbamoyl-2-methylpropyl}-carbamoyl-ethyl)-2-deoxy-D-glucose, 2-iso-butyroylamino-3-O-({L-1-[D-1-carbamoyl-3-(carboxy-methyl-carbamoyl)-propyl]-carbamoyl-ethyl}-carbamoyl-methyl)-2-deoxy-D-glucose, 2-iso-butyroylamino-3-O-({L-1-[D-1-carbamoyl-3-(carboxy-methyl-carbamoyl)-propyl]-carbamoyl-ethyl}-carbamoyl-methyl)-2-deoxy-D-glucose, 2-iso-butyroylamino-3-O-(D-1-{L-1-[D-1-carbamoyl-3-(carboxy-methyl-carbamoyl)-propyl]-carbamoyl-ethyl}-carbamoyl-ethyl)-2-deoxy-D-glucose, 2-iso-butyroylamino-3-O-({L-1-[D-1-carbamoyl-3-(L-1-carboxy-ethyl-carbamoyl)-propyl]-carbamoyl-ethyl}-carbamoyl-methyl)-2-deoxy-D-glucose, 2-iso-butyroylamino-3-O-(D-1-{L-1-[D-1-carbamoyl-3-(L-1-carboxy-ethyl-carbamoyl)-propyl]-carbamoyl-ethyl}-carbamoyl-ethyl)-2-deoxy-D-glucose, 2-iso-butyroylamino-3-O-({L-1-[D-1-carbamoyl-3-(L-1-carboxy-propyl-carbamoyl)-propyl]-carbamoyl-ethyl}-carbamoyl-methyl )-2-deoxy-D-glucose, 2-acetamino-3-O-({L-1-[D-1-carbamoyl-3-(carboxy-methyl-carbamoyl)-propyl]-carbamoyl-2-methylpropyl}-carbamoyl-methyl)-2-deoxy-D-glucose, 2-acetamino-3-O-(D-1-}L-1-[D-1-carbamoyl-3-(carboxy-methyl-carbamoyl)-propyl]-carbamoyl-2-methylpropyl}-carbamoyl-ethyl)-2-deoxy-D-glucose, 2-acetamino-3-O-({L-1-[D-1-carbamoyl-3-(L-1-carboxy-ethyl-carbamoyl)-propyl]-carbamoyl-2-methyl-propyl}-carbamoyl-methyl)-2-deoxy-D-glucose, 2-acetamino-3-O-(D-1-{L-1-[D-1-carbamoyl-3-(L-1-carboxy-ethyl-carbamoyl)-propyl]-carbamoyl-2-methylpropyl}-carbamoyl-ethyl)-2-deoxy-D-glucose, 2-acetamino-3-O-({L-1-[D-1-carbamoyl-3-(L-1-carboxy-propyl-carbamoyl)-propyl]-carbamoyl-2-methyl-propyl}-carbamoyl-methyl -2-deoxy-D-glucose, 2-butyroylamino-3-O-({L-1-[D-1-carbamoyl-3-(L-1-carboxy-butyl-carbamoyl)-propyl]-carbamoyl-ethyl}-carbamoyl-methyl)-2-deoxy-D-glucose, 2-acetamino-3-O-(D-1-{L-1-[D-1-carbamoyl-3-(L-1-carboxy-ethyl-carbamoyl)-propyl]-carbamoyl-propyl}-carbamoyl-ethyl -2-deoxy-D-glucose, 2-acetamino-3-O-({L-1-[D-1-carbamoyl-3-(L-1-carboxy-ethyl-carbamoyl)-propyl]-carbamoyl-propyl}-carbamoyl-methyl)-2-deoxy-D-glucose, 2-acetamino-3-O-(D-1-{L-1-[D-1-carbamoyl-3-(carboxy-methyl-carbamoyl)-propyl]-carbamoyl-propyl}-carbamoyl-ethyl)-2-deoxy-D-glucose, 2-acetamino-3-O-({L-1-[D-1-carbamoyl-3-(carboxy-methyl-carbamoyl)-propyl]-carbamoyl-propyl}-carbamoyl-methyl)-2-deoxy-glucose, 2-acetamino-3-O-({L-1-[D-1-carbamoyl-3-(L-1-carboxy-propyl-carbamoyl)-propyl]-carbamoyl-ethyl}-carbamoyl-methyl)-2-deoxy-D-glucose, 2-acetamino-3-O-(D-1-{L-1-[D-1-carbamoyl-3-(L-1-carboxy-propyl-carbamoyl)-propyl]-carbamoyl-ethyl}-carbamoyl-ethyl )-2-deoxy-D-glucose, 2-acetamino-3-O-({L-1-[D-1-carbamoyl-3-(L-1-carboxy-2-methylpropyl-carbamoyl)-propyl]-carbamoyl-ethyl}-carbamoyl-methyl )-2-deoxy-D-glucose, 2-acetamino-3-O-( D-1-{L-1-[D-1-carbamoyl-3-(L-1carboxy-2-methyl-propyl-carbamoyl)-propyl]-carbamoyl-ethyl}-carbamoyl-ethyl)-2-deoxy-D-glucose, 2-acetamino-3-O-({L-1-[D-1-carbamoyl-3-(L-1-carboxy-butyl-carbamoyl)-propyl]-carbamoyl-ethyl}-carbamoyl-methyl)-2-deoxy-D-glucose, 2-butyroylamino-3-O-({L-1-[D-1-carbamoyl-3-(carboxy-methyl-carbamoyl)-propyl]-carbamoyl-ethyl}-carbamoyl-methyl)-2-deoxy-D-glucose, 2-butyroylamino-3-O- D-1-{L-1-[D-1-carbamoyl-3-(L-1carboxy-propyl-carbamoyl)-propyl]-carbamoyl-ethyl}-carbamoyl-ethyl -2-deoxy-D-glucose, 2-butyroylamino-3-O-({L-1-[D-1-carbamoyl-3-(L-1-carboxy-propyl-carbamoyl)-propyl]-carbamoyl-ethyl}-carbamoyl-methyl -2-deoxy-D-glucose, 2-butyroylamino-3-O- D-1-{L-1-[D-1-carbamoyl-3-(L-1-carboxy-2-methyl-propyl-carbamoyl)-propyl]-carbamoyl-ethyl}-carbamoyl-ethyl)-2-deoxy-D-glucose, 2-butyroylamino-3-O-({L-1-[D-1-carbamoyl-3-(L-1-carboxy-2-methyl-propyl-carbamoyl)-propyl]-carbamoyl-ethyl}-carbamoyl-methyl)-2-deoxy-D-glucose, 2-benzoylamino-3-O-({L-1-[D-1-carbamoyl-3-(L-1-carboxy-ethyl-carbamoyl)-propyl]-carbamoyl-ethyl}-carbamoyl-methyl)-2-deoxy-D-glucose, 2-benzoylamino-3-O-(D-1-{L-1-[D-1-carbamoyl-3-(carboxy-methyl-carbamoyl)-propyl]-carbamoyl-ethyl}-carbamoyl-ethyl)-2-deoxy-D-glucose, 2-benzoylamino-3-O-({L-1-[D-1-carbamoyl-3(L-1-carboxy-ethyl-carbamoyl)-propyl]-carbamoyl-propyl}-carbamoyl-methyl)-2-deoxy-D-glucose, 2-benzoylamino-3-O-(D-1-{L-1-[D-1-carbamoyl-3-(carboxy-methyl-carbamoyl)-propyl]-carbamoyl-propyl}-carbamoyl-ethyl)-2-deoxy-D-glucose, 2-acetamino-3-O-({L-1-[D-1-carbamoyl-3-(L-1-carboxy-ethyl-carbamoyl)-propyl]-carbamoyl-N,N- tetramethylene}-carbamoyl-methyl)-2-deoxy-D-glucose, 2-acetamino-3-O-(D-1-{L-1-[D-1-carbamoyl-3-(L-1-carboxy-ethyl-carbamoyl)-propyl]-carbamoyl-N,N-tetramethylene}-carbamoyl-ethyl)-2-deoxy-D-glucose, 2-acetamino-3-O-({L-1-[D-1-carbamoyl-3-(carboxy-methyl-carbamoyl)-propyl]-carbamoyl-N,N-tetramethylene}-carbamoyl-methyl)-2-deoxy-D-glucose, 2-acetamino-3-O-(D-1-{L-1-[D-1-carbamoyl-3-(carboxy-methyl-carbamoyl)-propyl]-carbamoyl-N,N-tetramethylene}-carbamoyl-ethyl)-2-deoxy-D-glucose, 2-acetamino-3-O-({L-1-[D-1carbamoyl-3-(L-1-carboxy-ethyl-carbamoyl)-propyl]-carbamoyl-2-hydroxy-ethyl}-carbamoyl-methyl -2-deoxy-D-glucose, 2-acetamino-3-O-(D-1-{L-1-[D-1-carbamoyl-3-(L-1-carboxy-ethyl-carbamoyl)-propyl]-carbamoyl-2-hydroxy-ethyl}-carbamoyl-ethyl)-2-deoxy-D-glucose, 2-benzoylamino-3-O-({L-1-[D-1-carbamoyl-3-(L-1-carboxy-ethyl-carbamoyl)-propyl]-carbamoyl-2-hydroxy-ethyl}-carbamoyl-methyl)-2-deoxy-D-glucose, 2-benzoylamino-3-O-(D-1-{L-1-[D-1-carbamoyl-3-(L-1-carboxy-ethyl-carbamoyl)-propyl]-carbamoyl-2-hydroxy-ethyl}-carbamoyl-ethyl)-2-deoxy-D-glucose, 2-acetamino-3-O-({L-1-[D-1-carbamoyl-3-(L-1-carboxy-methyl)-carbamoyl-propyl]-carbamoyl-methyl}-carbamoyl-methyl)-2-deoxy-D-glucose, 2-acetamino-3-O-(D-1-{L-1-[D-1-carbamoyl-3-(L-carboxy-methyl-carbamoyl)-propyl]-carbamoyl-methyl}-carbamoyl-ethyl)-2-deoxy-D-glucose, 2-acetamino-3-O-({L-1-[D-1-carbamoyl-3-(L-1carboxy-methyl-carbamoyl)-propyl]-carbamoyl-methyl}-carbamoyl-methyl)-2-deoxy-D-glucose, 2-acetamino-3-O-(D-1-{L-1-[D-1-carbamoyl-3-(L-1-carboxy-methyl-carbamoyl)-propyl]-carbamoyl-methyl}-carbamoyl-ethyl-2-deoxy-D-glucose and 2-acetamino-3-O-({L-1-[D-1-carbamoyl-3-(L-1-carboxy-methyl-carbamoyl)-propyl]-carbamoyl-methyl}-carbamoyl-methyl)-2-deoxy-D-glucose.

EXAMPLE 39

A solution of 4.2 g of benzyl-2-acetamino-3-O-({[L-1-[D-1-carbamoyl-3-(L-5-benzyloxycarbonylamino-5-carbamoyl-pentyl-carbamoyl)-propyl]-carbamoyl-ethyl}-carbamoyl-methyl)-2-deoxy-α-D-glucopyranoside in 100 ml of a 2:1 mixture of methanol and water is hydrogenated in the presence of 0.5 g of 10% palladium/charcoal under normal pressure at room temperature. During the reaction, the pH of the reaction mixture is kept at 6 by addition of 1N hydrochloric acid. After the absorption of hydrogen has ceased, the catalyst is removed by filtration and the filtrate is evaporated to dryness. The residue is dissolved in a small amount of distilled water and freeze-dried. This gives 2-acetamino-3-O-({L-1-[D-1-carbamoyl-3-(L-5-amino-5-carbamoyl-pentyl-carbamoyl)-propyl]-carbamoyl-ethyl}-carbamoyl-methyl)-2-deoxy-D-glucose hydrochloride as a white powder.

The starting material used can be prepared as follows:

A solution of 15 g of α-carbobenzoxy-ε-t-butoxy-carbonyl-L-lysine methyl ester in 100 ml of a saturated solution of ammonia in methanol is left to stand for 48 hours at room temperature and then evaporated to dryness. The product, α-carbobenzoyl-ε-t-butoxycarbonyl-L-lysine-amide is recrystallised from methanol/ether; melting point 142° C., $[\alpha]_D^{20} = -3° \pm 1°$ (methanol, c=1.018).

A solution, cooled to 0° C., of 3 g of α-carbobenzoxy-ε-t-butoxycarbonyl-L-lysine-amide in 25 ml of trifluoroacetic acid is stirred for 1 hour and then evaporated to dryness. 20 ml of saturated sodium chloride solution and ice are added to the residue and the mixture is rendered alkaline with concentrated ammonia solution and extracted with ethyl acetate. The organic phase is then washed with saturated sodium chloride solution, dried over sodium sulfate and evaporated to dryness. This gives α-carbobenzoxy-L-lysine-amide as a white froth.

A solution of 5.6 g of benzyl-2-acetamino-3-O-({L-1-(D-1-carbamoyl-3-carboxy-propyl)-carbamoyl-ethyl}-carbamoyl-methyl)-2-deoxy-α-D-glucopyranoside and 2.8 g of α-carbobenzoxy-L-lysine-amide in 30 ml of N,N-dimethyl-formamide is treated with 1.1 g of N-hydroxysuccinimide and 2.2 g of dicyclohexylcarbodiimide and the mixture is stirred for 40 hours at room temperature. The dicyclohexylurea which has crystallised out is filtered off with suction and washed with 10 ml of N,N-dimethylformamide. The filtrate is evaporated to dryness and the residue is extracted for 30 minutes with 100 ml of distilled water. The undissolved material is filtered off with suction, washed with water and dried; it constitutes benzyl-2-acetamino-3-O-({L-1-[D-1-carbamoyl-3-(L-5-benzyloxy-carbonylamino-5-carbamoyl-pentyl-carbamoyl)-propyl]-carbamoyl-ethyl}-carbamoyl-methyl)-2-deoxy-α-D-glucopyranoside. The product is recrystallised from methanol/ethyl acetate.

2-Acetamino-3-O-({L-1-[D-1-carbamoyl-3-(5-amino-L-1-carbamoyl-pentyl-carbamoyl)-propyl]-carbamoyl-ethyl}-carbamoyl-methyl)-2-deoxy-D-glucose hyrochloride is prepared analogously.

EXAMPLE 40

A solution of 2.8 g of benzyl-3-O-{[L-1-(D-1-carbamoyl-3-carboxy-propyl)-carbamoyl-propyl]-carbamoyl-methyl}-2-deoxy-2-isobutyroylamino-α-D-glucopyranoside in 80 ml of a 1:1 mixture of methanol and distilled water is hydrogenated in the presence of 0.3 g of 10% palladium/charcoal under normal pressure at 45° C. After working up and freeze-drying the residue, 3-O-{[L-1-(D-1-carbamoyl-3-carboxy-propyl)-carbamoyl-propyl]-carbamoyl-methyl}-2-deoxy-2-isobutyroylamino-D-glucose is obtained as a white powder.

The starting material used is prepared as follows:

A mixture of the solutions of 21.0 g of benzyl-2-amino-2-deoxy-4,6-O-isopropylidene-α-D-glucopyranoside in 150 ml of chloroform and 9.0 g of potassium bicarbonate in 150 ml of distilled water is cooled to 0° C., with stirring, and is treated dropwise with 8.5 ml of isobutyric acid chloride. After the mixture has been stirred for 1 hour at room temperature, the organic phase is seperated off, washed with ice-cold 0.5N hydrochloric acid, with water, with a saturated sodium bicarbonate solution and again with water, dried and evaporated. The product, benzyl-2-deoxy-2-isobutylamino-4,6-O-isopropylidene-α-D-glucopyranoside, is crystallised from 150 ml of ether; melting point 82° C., $[\alpha]_D^{20} = +109° \pm 1°$ (chloroform, c=1.017).

A solution of 15.1 g of benzyl-2-deoxy-2-isobutyroylamino-4,6-O-isopropylidene-α-D-glucopyranoside in 150 ml of absolute acetonitrile is treated with 1.9 g of sodium hydride (Fluka, pract.) in a nitrogen atmosphere, with exclusion of moisture and with stirring; the reaction mixture is then stirred for 1.5 hours at 40° C. Thereafter, it is cooled to −10° C. and treated with 5.6 ml of methyl bromoacetate. The batch is then stirred for 15 minutes in an ice bath and for 2 hours at room temperature. After working up, benzyl-2-deoxy-2-isobutyl-amino-4,6-O-isopropylidene-3-O- methoxycarbonyl-methyl-α-D-glucopyranoside is obtained; this material is recrystallised from ether/petroleum ether; melting point 119°-120° C., $[\alpha]_D^{20} = +152° \pm 1°$ (chloroform, c=0.963).

A solution of 3.16 g of benzyl-2-deoxy-2-isobutyroylamino-4,6-O-isopropylidene-3-O-methoxycarbonylmethyl-α-D-glucopyranoside in 30 ml of methanol and 10 ml of 1N sodium hydroxide solution is left to stand for 1 hour at room temperature. 3 ml of 1N hydrochloric acid are added and the solution is evaporated to dryness. The residue is dissolved in 50 ml of N,N-dimethylformamide and the solution is treated with 2.26 g of L-α-amino-butyroyl-D-isoglutamine tert.-butyl ester hydrochloride and 1.75 g of EEDQ and is left to stand for 24 hours at room temperature. A further 0.2 g of EEDQ is added and the mixture is left to stand for a further 24 hours. The solvent is distilled off and the residue is dissolved in ethyl acetate/water. The organic phase is separated off and washed with ice-cold 1N hydrochloric acid, with water, with a saturated sodium bicarbonate solution and with water, and is dried over sodium sulfate and then evaporated to dryness. This gives benzyl-3-O-{[L-1-(D-1-carbamoyl-3-carboxy-propyl)-carbamoyl-propyl]-carbamoyl-methyl}-2-deoxy-2-isobutylamino-4,6-O-isopropylidene-α-D-glucopyranoside tert.-butyl ester as a white froth.

This product is dissolved in 60 ml of glacial acetic acid, 60 ml of water are added with stirring, and the solution is left to stand for 24 hours at room temperature. It is then evaporated to dryness in a waterpump vacuum and the residue is dissolved in ethanol. The solution is filtered in the presence of active charcoal and is again evaporated to dryness. This gives benzyl-3-O-{[L-[D-1-carbamoyl-3-carboxy-propyl)-carbamoyl-propyl]-carbamoyl-methyl}-2-deoxy-2-isobutyroylamino-α-D-glucopyranoside tert.-butyl ester as a white amorphous material of $[\alpha]_D^{20} = +74° \pm 1°$ (methanol, c=0.950).

A solution, cooled to 0° C., of 3.9 g of this tert.-butyl ester in 40 ml of 98% trifluoroacetic acid is stirred for 1 hour at 0° C. and poured into 500 ml of absolute ether. The product which has crystallised out is filtered off with suction, washed with ether and dried in vacuo. The resulting powder is dissolved in 40 ml of a 1:1 water/tetrahydrofuran mixture and the solution is stirred for 30 minutes with 50 ml of Dowex 3 ion exchanger resin (acetate form). The ion exchanger is filtered off and washed with 500 ml of tetrahydrofuran/1N acetic acid. The filtrate is evaporated to dryness and the product is crystallised from methanol/ether, melting point 205°-206° C.

EXAMPLE 41

A solution of 3.1 g of benzyl-3-O-{[L-1-(D-1-carbamoyl-3-carboxy-propyl)-carbamoyl-ethyl]-carbamoyl-methyl}-2-deoxy-2-isobutyroylamino-α-D-glucopyranoside in 40 ml of a 1:1 methanol/water mixture is hydrogenated in the presence of 10% palladium/charcoal under normal pressure at 45° C. After working up, 3-O-{[L-1-(D-1-carbamoyl-3-carboxy-propyl)-carbamoyl-ethyl]-carbamoyl-methyl}-2-deoxy-2-isobutyroylamino-D-glucose is obtained as a white powder by freeze-drying.

The method of preparation of the starting material used is analogous to that described in Example 40:

The condensation of the sodium salt of benzyl-3-O-carboxy-methyl-2-deoxy-2-isobutyroylamino-4,6-O-isopropylidene-α-D-glucopyranoside with L-alanyl-D-isoglutamine tert.-butyl ester hydrochloride gives benzyl-3-O-{[L-1-(D-1-carbamoyl-3-carboxy-propyl)-carbamoyl-ethyl]-carbamoyl-methyl}-2-deoxy-2-isobutyroylamino-4,6-O-isopropylidene-α-D-glucopyranoside tert.-butyl ester as a white froth. The hydrolysis of the 4,6-O-isopropylidene group gives benzyl-3-O-{[L-1-(D-1-carbamoyl-3-carboxypropyl)-carbamoyl-ethyl]-carbamoyl-methyl}-2-deoxy-2-isobutyroylamino-α-D-glucopyranoside tert.-butyl ester of $[\alpha]_D^{20} = +71° \pm 1°$ (methanol, c=0.956).

The tert.-butyl ester is split with trifluoroacetic acid. This gives benzyl-3-O-{[L-1-(D-1-carbamoyl-3-carboxy-propyl)-carbamoyl-ethyl]-carbamoyl-methyl}-2-deoxy-2-isobutyroylamino-α-D-glucopyranoside as a white amorphous product.

EXAMPLE 42

A solution of 4.2 g of benzyl-2-acetyl-N-methylamino-3-O-{[L-1-(D-1-carbamoyl-3-carboxy-propyl)-carbamoyl-ethyl]-carbamoyl-methyl}-2-deoxy-D-glucopyranoside in 75 ml of a 1:1 methanol/water mixture is hydrogenated in the presence of 0.5 g of 10% palladium/charcoal under normal pressure at 45° C. The catalyst is filtered off and the filtrate is evaporated to dryness. The residue is dissolved in a small amount of distilled water and freeze-dried. This gives 2-acetyl-N-methyl-amino-3-O-{[L-1-(D-1-carbamoyl-3-carboxy-propyl)-carbamoylethyl]-carbamoyl-methyl}-2-deoxy-D-glucose as a white powder.

The starting material used is prepared as follows:

A solution of 8.5 g of benzyl-2-acetamino-2-deoxy-4,6-O-isopropylidene-3-O-methoxycarbonylmethyl-α-D-glucopyranoside in 80 ml of absolute acetonitrile is treated with 0.75 g of sodium hydride (Fluka, pract.) in a nitrogen atmosphere, with stirring and exclusion of moisture, and the mixture is then stirred for 1 hour at 40° C. Thereafter, the reaction mixture is cooled to room temperature and is treated dropwise, in the course of 4 hours, with a solution of 6.0 g of methyl iodide in 50 ml of absolute acetonitrile. After a further 3 hours, the reaction mixture is filtered and the filtrate is evaporated to dryness. The residue is dissolved in ethyl acetate and this solution is washed with water, dried over sodium sulfate and evaporated to dryness. This gives benzyl-2-acetyl-N-methyl-amino-2-deoxy-4,6-O-isopropylidene-3-O-methoxy-carbonyl-methyl-α-D-glucopyranoside as a yellow oil of Rf value 0.45 on thin layer silica gel plates using the system methylene chloride/ethyl acetate 85:15.

A solution of 4.4 g of benzyl-2-acetyl-N-methylamino-2-deoxy-4,6-O-isopropylidene-3-O-methoxycarbonyl-methyl-α-D-glucopyranoside in 60 ml of methanol and 15 ml of 1N sodium hydroxide solution is left to stand for 1 hour at room temperature, after which it is treated with 5 ml of 1N hydrochloric acid and evaporated to dryness. The resulting sodium salt of benzyl-2-acetyl-N-methyl-amino-3-O-carboxymethyl-2-deoxy-4,6-O-isopropylidene-α-D-glucopyranoside is dissolved in 50 ml of N,N-dimethylformamide and condensed with 3.2 g of L-alanyl-D-isoglutamine tert.-butyl ester hydrochloride in the presence of 2.5 g of EEDQ. The solution is evaporated to dryness in vacuo and the residue is dissolved in ethyl acetate. This solution is washed with water, ice-cold 1N hydrochloric acid, water, a saturated sodium bicarbonate solution and water, and is dried over magnesium sulfate and evaporated to dryness. This gives benzyl-2-acetyl-N-methyl-amino-3-O-{[L-1-(D-1-carbamoyl-3-carboxy-propyl)-carbamoylethyl]-carbamoyl-methyl}-2-deoxy-4,6-O-isopropylidene-α-D-glucopyranoside tert.-butyl ester as a yellowish froth. This product is dissolved in 45 ml of 95% trifluoroacetic acid which has been pre-cooled to 0° C., and the solution is stirred for 1 hour at 0° C. The reaction mixture is poured into 400 ml of absolute ether and the product which has precipitated is filtered off with suction, washed with ether and dried. Treatment of this substance with Dowex-3 ion exchanger resin in the acetate form gives benzyl-2-acetyl-N-methyl-amino-3-O-{[L-1-(D-1-carbamoyl-3-carboxy-propyl)-carbamoyl-ethyl]-carbamoyl-methyl}-2-deoxy-α-D-glucopyranoside, free from trifluoroacetic acid, as a white powder.

The following are prepared analogously: 2-acetyl-N-methyl-amino-3-O-{D-1-[L-1-(D-1-carbamoyl-3-carboxy-propyl)-carbamoyl-ethyl]-carbamoyl-ethyl}-2-deoxy-D-glucose, 2-acetyl-N-methyl-amino-3-O-{D-1-[L-1-(D-1-carbamoyl-3-carboxy-propyl)-carbamoyl-propyl]-carbamoyl-ethyl}-2-deoxy-D-glucose, 2-acetyl-N-methyl-amino-3-O-{[L-1-(D-1-carbamoyl-3-carboxy-propyl)-carbamoyl-propyl]-carbamoyl-methyl}-2-deoxy-D-glucose, 2-acetyl-N-methyl-amino-3-O-{[L-1-(D-1-carbamoyl-3-carboxy-propyl)-carbamoyl-2-methyl-propyl]-carbamoyl-methyl}-2-deoxy-D-glucose, 2-acetyl-N-methyl-amino-3-O-{D-1-[L-1-(D-1-carbamoyl-3-carboxy-propyl)-carbamoyl-2′-methyl-propyl]-carbamoyl-ethyl}-2-deoxy-D-glucose, 3-O-{[L-1-(D-1-carbamoyl-3-carboxy-propyl)-carbamoyl-ethyl]-carbamoyl-methyl}-2-deoxy-2-propionyl-N-methyl-amino-D-glucose and 2-butyryl-N-methyl-amino-3-O-{[L-1-(D-1-carbamoyl-3-carboxy-propyl)-carbamoyl-ethyl]-carbamoyl-methyl}-2-deoxy-D-glucose.

EXAMPLE 43

The trimethylsilyl ethers can be prepared, for example, as follows:

0.3 g of 2-benzamido-2-deoxy-3-O-{[L-1-(D-1-carbamoyl-3-carboxypropyl)-carbamoyl-ethyl]-carbamoyl-methyl}-D-glucose is dissolved in 3 ml of dimethylformamide and treated with 0.4 ml of bis-trimethylsilylacetamide. After 5 hours at 35°, the mixture is evaporated in vacuo to leave a syrup, from which acetamide formed can be removed by dissolving the product in absolute ether or absolute ethyl acetate. After renewed evaporation, a colourless syrup with $[\alpha]_D^{20}=+15°$ (c=0.8, dioxane) is obtained.

Syrupy 2-acetamino-2-deoxy-3-O-{[L-1-(D-1-carbamoyl-3-trimethylsilyl-carboxy-propyl)-carbamoylethyl]-carbamoylmethyl}-1,4,6-tri-trimethylsilyl-D-glucose, with $[\alpha]_D^{20}=-10°$ (c=0.91, dioxane), is obtained analogously.

On contact with water, the trimethylsilyl ester group is rapidly hydrolysed, so that these derivatives are also suitable for coupling.

EXAMPLE 44

A 5% solution of benzyl-2-acetamido-3-O-{{L-1-[D-1-(L-1-carboxy-ethyl)-carbamoyl-3-carboxypropyl]-carbamoyl-ethyl}-carbamoyl-methyl}-2-deoxy-α-D-glucopyranoside in a 2:1 tetrahydrofuran/water mixture is hydrogenated in the presence of 10% palladium on charcoal under normal pressure at room temperature. After the theoretical amount of hydrogen has been absorbed, the catalyst is filtered off and the filtrate is freeze-dried. This gives 2-acetamido-3-O-{{L-1-[D-1-(L-1-carboxy-ethyl)-carbamoyl-3-carboxypropyl]-carbamoyl-ethyl}-carbamoyl-methyl}-2-deoxy-D-glucose as a white powder. Rf value in a thin layer chromatogram=0.21 (ethyl acetate/n-butanol/pyridine/acetic acid/water=42:21:21:6:10).

The derivative with genuine muramic acid is obtained analogously.

The starting material can be prepared as follows:

5.68 g of N-tert.-butoxycarbonyl-L-alanyl-D-γ-benzyl-glutamyl-L-alanine benzyl ester are dissolved in a mixture of 5 ml of trifluoroacetic acid and 5 ml of 1,2-dichloroethane and the solution is left to stand for 16 hours at room temperature, with exclusion of moisture. The solution is then diluted with 50 ml of tetrahydrofuran, cooled in an ice bath and neutralised with trethylamine. After adding a solution of 3.7 g of benzyl-2-acetamido-3-carboxymethyl-2-deoxy-α-D-glucopyranoside and 1.38 ml of triethylamine in 100 ml of tetrahydrofuran, the batch is treated with 2.6 g of 2-ethoxy-N-ethoxycarbonyl-1,2-dihydroquinoline and left to stand for 24 hours at room temperature. After evaporating off the solvent, the residue is dissolved in a 9:1 chloroform/methanol mixture, the solution is washed with water, ice-cold 2N hydrochloric acid, water, a saturated sodium bicarbonate solution and water and is filtered, and the solvent is removed. This gives benzyl-2-acetamido-3-O-{{L-1-[D-1-(L-1-carboxy-ethyl)-carbamoyl-3-carboxy-propyl]-carbamoylethyl}-carbamoyl-methyl}-2-deoxy-α-D-glucopyranoside as a colourless powder, Rf value=0.48 (in the identical system).

The starting material used can be prepared as follows:

7.15 g of N-tert.-butoxycarbonyl-L-alanyl-D-glutamic acid γ-benzyl ester and 6.15 g of L-alanine benzyl ester p-toluenesulfonate are dissolved in 100 ml of anhydrous dimethylformamide. The solution is cooled in an ice bath and 4.03 g of N-hydroxysuccinimide, 3.61 g of dicyclohexylcarbodiimide and, finally, 1.95 ml of N-methylmorpholine are added successively, with stirring. After having been stirred for 6 hours at 0° and 15 hours at room temperature, the suspension is cooled, the precipitate (dicyclohexylurea and morpholine hydrochloride) is filtered off and the filtrate is evaporated. The residue is taken up in ethyl acetate and the solution is repeatedly washed with water, 1N citric acid and 1N sodium bicarbonate solution and again with water. The ethyl acetate solution is dried and evaporated and the crystalline residue is recrystallised from a 1:1 mixture of ethyl acetate and petroleum ether; melting point 135°-136°, $[\alpha]_D^{20}=-9°\pm1°$ (c=1, methanol), Rf value=0.82 (in the above system) and 0.86 (in a 3:1 mixture of acetontrile/water).

Instead of using alanine, the protected dipeptide can be lengthened analogously with other natural L-aminoacids.

EXAMPLE 45

$7.5\times10^8$ killed trypanosoma cruzi parasites [pathogens of Chagas disease] are suspended in a solution of 50 mg of 2-acetamino-3-O-{[L-1-(D-carbamoyl-3-carboxy-propyl)-carbamoylethyl]-carbamoylmethyl}-2-deoxy-D-glucose N-hydroxysuccinimide ester in 6 ml of physiological buffer solution. The suspension is incubated for two hours at 37° C. The parasites conjugated with the muramyl-dipeptide are then sedimented by centrifuging. The sediment is washed by resuspending it in physiological buffer solution and again centrifuging. The washed parasite/muramyl-dipeptide conjugates are suspended in physiological buffer solution and used for immunisation.

The quantitative determination of muramyl-dipeptide coupled to the trypanosomes is carried out as described in Example 1, by means of the Morgan-Elson reaction, and indicates 50–70 mg of muramyl-dipeptide per mg of trypanosomes.

What is claimed is:

1. A muramyl-peptide of the general formula

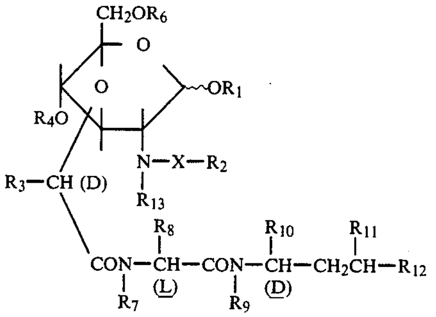

(II)

in which X is a carbonyl group, $R_1$, $R_4$ and $R_6$ are tri-lower alkyl-silyl, $R_2$ is unsubstituted or substituted alkyl or carbocyclic aryl, $R_3$ is hydrogen or alkyl, $R_7$ and $R_{13}$ are hydrogen or lower alkyl, $R_8$ is hydrogen, lower alkyl, free, esterified or etherified hydroxy-lower alkyl, free, esterified or etherified mercapto-lower alkyl, free or acylated amino-lower alkyl, cycloalkyl having 5 or 6 carbon atoms, cycloalkyl-lower alkyl, of which the cycloalkyl radical contains 5 or 6 carbon atoms, unsubstituted or substituted aryl or aralkyl, nitrogen-containing heterocyclyl or heterocyclyl-lower alkyl, $R_7$ and $R_8$ together can also be alkylene having 3 or 4 carbon atoms, $R_9$ is hydrogen or lower alkyl, the radicals $R_{10}$ and $R_{12}$ independently of one another are a carboxyl radical which may or may not be esterified or amidised, and $R_{11}$ is hydrogen or a carboxyl radical which may or may not be esterified or amidised.

2. A compound according to claim 1 in which $R_2$ represents alkyl having 1 to 18 carbon atoms which is unsubstituted or substituted by hydroxy, lower alkoxy, lower alkanoyloxy, halogen, mercapto, lower alkylmercapto, lower alkanoylmercapto, carboxy, lower alkoxycarbonyl and/or carbamoyl, or represents phenyl which is unsubstituted or substituted by lower alkyl, hydroxy, lower alkoxy, lower alkanoyl, lower alkylenedioxy, halogen and/or trifluoromethyl, $R_3$, $R_7$, $R_9$ and $R_{13}$ are independently of one another hydrogen or lower alkyl, $R_8$ is hydrogen, lower alkyl which is unsubstituted or substituted by hydroxy, lower alkoxy, lower alkanoyloxy, mercapto, lower alkylmercapto, lower alkanoylmercapto, amino, lower alkanoylamino, carbamoylamino or cycloalkyl having 5 or 6 carbon atoms, or represents cycloalkyl having 5 or 6 carbon atoms, phenyl or phenyl-lower alkyl, in which the phenyl radicals are unsubstituted or substituted as defined above, or heterocyclyl or heterocyclyl-lower alkyl wherein the heterocyclyl radicals are 5- or 6-membered, contain one or two nitrogen atoms in the ring and may or may not contain a fused phenyl radical, $R_7$ and $R_8$ together can also represent alkylene having 3 or 4 carbon atoms, $R_{10}$ and $R_{12}$ independently of one another represent carboxyl, lower alkoxycarbonyl, tri-lower alkylsilyloxycarbonyl or carbamoyl which is unsubstituted or mono- or disubstituted at the nitrogen atom by unsubstituted or carboxy- or carbamoyl-substituted lower alkyl or by phenyl, benzyl, tetramethylene or pentamethylene or $R_{11}$ represents, independently, the same groups as $R_{10}$ and $R_{12}$ or hydrogen.

3. A compound according to claim 1 wherein $R_{13}$ represents hydrogen.

4. A compound according to claim 2 wherein $R_3$, $R_7$, and $R_{13}$ are hydrogen, and $R_2$ is lower alkyl which is unsubstituted or substituted by hydroxyl or lower alkoxy, or is phenyl which is unsubstituted or substituted by hydroxy, lower alkoxy, lower alkyl or halogen.

5. A compound according to claim 2 wherein $R_7$ and $R_{13}$ are hydrogen, $R_2$ is lower alkyl which is unsubstituted or substituted by hydroxyl or lower alkoxy or is phenyl which is unsubstituted or substituted by hydroxyl, lower alkoxy, lower alkyl or halogen, and $R_3$ is methyl.

6. a compound according to claim 2 wherein $R_7$, $R_9$ and $R_{13}$ are hydrogen, $R_2$ is lower alkyl which is unsubstituted or substituted by hydroxyl or methoxy or is phenyl which is unsubstituted or substituted by hydroxyl, methoxy, methyl, ethyl or halogen, $R_3$ is hydrogen or methyl, $R_8$ is benzyl, p-hydroxybenzyl, phenyl or lower alkyl which is unsubstituted or substituted or lower alkylmercapto or hydroxy, and $R_{10}$ and $R_{12}$ are, independently, carboxyl, lower alkoxycarbonyl or carbamoyl and $R_{11}$ represents, independently, the same groups as $R_{10}$ and $R_{12}$ or hydrogen.

7. A compound according to claim 2 wherein $R_{13}$ is hydrogen, $R_2$ is lower alkyl which is unsubstituted or substitured by hydroxyl or methoxy or is phenyl which is unsubstituted or substituted by hydroxyl, methoxy, methyl, ethyl or halogen, $R_3$ and $R_9$ are hydrogen or methyl, $R_8$ is methyl, ethyl, n-propyl, i-propyl, 2-methyl-propyl, methylmercaptomethyl, hydroxymethyl, hydroxyethyl, phenyl, benzyl or p-hydroxybenzyl and $R_{10}$ and $R_{12}$ are carboxyl, lower alkoxycarbonyl or carbamoyl and $R_{11}$ represents the same groups as $R_{10}$ and $R_{12}$ or hydrogen.

8. A compound according to claim 2 wherein $R_7$ and $R_8$ together are propylene or butylene.

9. A compound according to claim 2 wherein $R_{11}$ is hydrogen.

10. A compound according to claim 2 wherein $R_{11}$ and $R_{13}$ are hydrogen, $R_2$ is methyl, ethyl or phenyl, $R_3$ is hydrogen or methyl, $R_7$ is hydrogen, methyl, ethyl or n-propyl, $R_8$ is methyl, ethyl or isopropyl, $R_9$ is hydrogen or methyl, $R_{10}$ is carboxyl, carbamoyl, N-(carbamoylmethyl)-carbamoyl or N-(1-carboxyethyl)-carbamoyl and $R_{12}$ is carboxy or N-(1-carboxy-ethyl)-carbamoyl.

11. A compound according to claim 1, which is 2-acetamido-3-O-{[L-1-(D-1-carbamoyl-3-trimethylsilyloxycarbonyl-propyl)-carbamoyl-ethyl]-carbamoylmethyl}-2-deoxy-1,4,6-O-tris-trimethylsilyl-D-glucose.

12. A compound according to claim 1, which is 2-benzamido-3-O-{[L-1-(D-1-carbamoyl-3-trimethylsilyloxycarbonylpropyl)-carbamoyl-ethyl]-carbamoylmethyl}-2-deoxy-1,4,6-O-tris-trimethylsilyl-D-glucose.

13. A compound according to claim 2, wherein $R_1$, $R_4$ and $R_6$ each represent trimethylsilyl.

14. A compound according to claim 6, wherein $R_1$, $R_4$ and $R_6$ each represent trimethylsilyl.

15. A compound according to claim 7, wherein $R_1$, $R_4$ and $R_6$ each represent trimethylsilyl.

* * * * *